US00RE48404E

(19) United States
(12) Reissued Patent
Kim et al.

(10) Patent Number: US RE48,404 E
(45) Date of Reissued Patent: *Jan. 26, 2021

(54) HYBRID HEPATOCYTE GROWTH FACTOR GENE HAVING HIGH EXPRESSION EFFICIENCY OF TWO HETEROTYPES OF HEPATOCYTE GROWTH FACTOR

(71) Applicant: Helixmith Co., Ltd, Seoul (KR)

(72) Inventors: Jong-Mook Kim, Seoul (KR); Woong Hahn, Goyang (KR); Eun-Jin Park, Seoul (KR)

(73) Assignee: Helixmith Co., Ltd, Seoul (KR)

( * ) Notice: This patent is subject to a terminal disclaimer.

(21) Appl. No.: 15/642,307

(22) Filed: Jul. 5, 2017

Related U.S. Patent Documents

Reissue of:
(64) Patent No.: 7,745,174
Issued: Jun. 29, 2010
Appl. No.: 12/650,860
Filed: Dec. 31, 2009

U.S. Applications:
(60) Division of application No. 10/944,277, filed on Sep. 20, 2004, now Pat. No. 7,812,146, which is a continuation of application No. PCT/KR03/00548, filed on Mar. 20, 2003.

(30) Foreign Application Priority Data

Mar. 20, 2002 (KR) ..... 10-2002-0015074

(51) Int. Cl.
*C07K 14/475* (2006.01)

(52) U.S. Cl.
CPC ..... *C07K 14/4753* (2013.01)

(58) Field of Classification Search
CPC ..... A61P 1/16; C07K 14/4753
See application file for complete search history.

(56) References Cited

U.S. PATENT DOCUMENTS

| | | | | |
|---|---|---|---|---|
| 5,328,836 | A | 7/1994 | Shima et al. | |
| 5,500,354 | A | 3/1996 | Kitamura et al. | |
| 5,580,859 | A | 12/1996 | Felgner et al. | |
| 5,587,359 | A | 12/1996 | Higashio et al. | |
| 5,652,225 | A | 7/1997 | Isner | |
| 5,693,622 | A | 12/1997 | Wolff et al. | |
| 6,013,624 | A | 1/2000 | Goldberg et al. | |
| 6,121,246 | A | 9/2000 | Isner | |
| 6,248,722 | B1 | 6/2001 | Morishita et al. | |
| 6,258,787 | B1 | 7/2001 | Isner | |
| 6,316,419 | B1 | 11/2001 | Leiden et al. | |
| 6,413,942 | B1 | 7/2002 | Felgner et al. | |
| 6,498,144 | B1 | 12/2002 | Goldberg et al. | |
| 6,706,694 | B1 | 3/2004 | Wolff et al. | |
| 6,887,477 | B1 | 5/2005 | Nagano et al. | |
| 7,285,540 | B2 | 10/2007 | Morishita et al. | |
| 7,745,174 | B2 | 6/2010 | Kim et al. | |
| 7,812,146 | B2 | 10/2010 | Kim et al. | |
| 7,838,505 | B2 * | 11/2010 | Kim | A61P 1/16 514/44 R |
| 8,338,385 | B2 * | 12/2012 | Kim | A61P 1/16 514/44 R |
| 8,389,492 | B2 * | 3/2013 | Kim | A61P 1/16 514/44 R |
| 2002/0172663 | A1 | 11/2002 | Palasis | |
| 2003/0148968 | A1 | 8/2003 | Hammond et al. | |
| 2003/0171287 | A1 | 9/2003 | Morishita et al. | |
| 2004/0105882 | A1 | 6/2004 | Morishita et al. | |
| 2004/0228834 | A1 | 11/2004 | Isner et al. | |
| 2005/0079581 | A1 | 4/2005 | Kim et al. | |
| 2006/0286072 | A1 | 12/2006 | Giordano et al. | |
| 2007/0059288 | A1 | 3/2007 | Dinsmore et al. | |
| 2008/0268030 | A1 | 10/2008 | Morishita et al. | |
| 2009/0004260 | A1 | 1/2009 | Morishita et al. | |
| 2009/0082293 | A1 | 3/2009 | Giordano et al. | |
| 2009/0131350 | A1 | 5/2009 | Kim et al. | |
| 2009/0202606 | A1 | 8/2009 | Kim et al. | |
| 2009/0258932 | A1 | 10/2009 | Kim et al. | |

FOREIGN PATENT DOCUMENTS

| | | |
|---|---|---|
| JP | 11-246433 | 9/1999 |
| KR | 2003-0075718 A | 9/2003 |
| WO | WO 98/50079 | 11/1998 |
| WO | WO 98/50079 A2 | 11/1998 |
| WO | WO 99/45775 | 9/1999 |
| WO | WO 99/45775 A1 | 9/1999 |
| WO | WO 01/34208 | 5/2001 |
| WO | WO 01/34208 A1 | 5/2001 |

(Continued)

OTHER PUBLICATIONS

Folkman (Circulation. vol. 97, Issue 12, pp. 1108-1110). Mar. 31, 1998.*
Courtney et al. (GenBank Accession No. AC004960 available since Jun. 12, 1998, Retrieved from Internet: http://www.ncbi.nlm.nih.gov/entrez/viewer.fcgi?db=nuccore&id=3845412).
European Search Report for European Application No. EP 03 74 4561, dated Apr. 18, 2006, European Patent Office, Munich, Germany.
Office Action for U.S. Appl. No. 10/944,277, dated Jan. 9, 2008.
Office Action for U.S. Appl. No. 10/944,277, dated Feb. 13, 2009.
Notice of Allowance and Fees Due for U.S. Appl. No. 10/944,277, dated May 29, 2009.
Notice of Allowance and Fees Due for U.S. Appl. No. 10/944,277, dated Oct. 23, 2009.
Office Action for U.S. Appl. No. 11/957,170, dated Jan. 28, 2010.
Esp@cenet Database, English language abstract of JP 11-246433 A, published Sep. 14, 1999 (listed as document B1 on the accompanying form PTO/SB/08A).
Romano et al. Stem Cells, 1999, 17 :191-202.

(Continued)

*Primary Examiner* — Padmashri Ponnaluri
(74) *Attorney, Agent, or Firm* — Fenwick & West LLP

(57) ABSTRACT

The present invention relates to a hybrid Hepatocyte Growth Factor (HGF) gene which is prepared by inserting an inherent or foreign intron between exons 4 and 5 in HGF cDNA, which has a base sequence of SEQ ID NO: 2. The gene has high expression efficiency and simultaneously expresses two heterotypes of HGF and dHGF (deleted variant HGF). Further the gene may be used for treating or preventing ischemic or liver diseases.

18 Claims, 12 Drawing Sheets

Specification includes a Sequence Listing.

(56) References Cited

FOREIGN PATENT DOCUMENTS

| | | |
|---|---|---|
| WO | WO 02/089856 | 11/2002 |
| WO | WO 02/089856 A1 | 11/2002 |

OTHER PUBLICATIONS

Liu et al, Journal of Controlled Release vol. 78, Issues 1-3, Jan. 17, 2002, pp. 259-266.
Schmitz et al, Gut. Jan. 2002; 50(1): 130-135.
U.S. Appl. No. 12/650,860, inventors Kim et al., filed Dec. 31, 2009.
Notice of Allowance and Fees Due for U.S. Appl. No. 12/650,860, dated Mar. 10, 2010.
Gardilik, et al., "Vectors and delivery systems in gene therapy," Med Sci Monit 11(4):RA110-121 (2005).
Kato et al., "Nonviral HVJ (hemagglutinating virus of Japan) liposome-mediated retrograde gene transfer of human hepatocyte growth factor into rat nervous system promotes functional and histological recovery of the crushed nerve," Neuroscience Research, 52, pp. 299-310, Elsevier Ireland Ltd and the Japan Neuroscience Society (2005).
Patil, et al., "DNA-based Therapeutics and DNA Delivery Systems: A Comprehensive Review," The AAPS Journal 9(1) Article 9:E61-E77 (2005).
Thomas, et al., "Progress and Problems with the use of viral vectors for gene therapy," Nature Reviews Genetics 4:346-358, Nature Publishing Group (2003).
Yang, et al., "Sustained Expression of Naked Plasmid DNA Encoding Hepatocyte Growth Factor in Mice Promotes Liver and Overall Body Growth," Hepatology 33:848-859, American Assoc. for the Study of Liver Disease (2001).
Notice of Allowance for U.S. Appl. No. 11/957,170 (now U.S. Pat. No. 7,838,505), dated Jul. 19, 2010.
Office Action for U.S. Appl. No. 12/359,137, dated Apr. 28, 2011.
Office Action for U.S. Appl. No. 12/421,425, dated Aug. 19, 2010.
Office Action for U.S. Appl. No. 12/421,425, dated Dec. 17, 2010.
U.S. Appl. No. 13/045,460, filed Mar. 10, 2011.
File History of U.S. Appl. No. 12/650,860, filed Dec. 31, 2009, Inventors: Jong-Mook Kim et al.
File History of U.S. Appl. No. 11/957,170, filed Dec. 14, 2007, Inventors: Jong-Mook Kim et al.
File History of U.S. Appl. No. 10/944,277, filed Sep. 20, 2004, Inventors: Jong-Mook Kim et al.
File History of U.S. Appl. No. 12/908,765, filed Oct. 20, 2010, Inventors: Jong-Mook Kim et al.
PCT International Search Report, PCT Application No. PCT/KR2003/000548, Sep. 5, 2003, 3 pages.
Shi, E. et al., "Nonviral Gene Transfer of Hepatocyte Growth Factor Attenuates Neurologic Injury After Spinal Cord Ischemia in Rabbits," Cardiopulmonary Support and Physiology, The Journal of Thoracic and Cardiovascular Surgery, Oct. 2006, pp. 941-947, vol. 132, No. 4.
Morishita, R. et al., "Safety Evaluation of Clinical Gene Therapy Using Hepatocyte Growth Factor to Treat Peripheral Arterial Disease," Hypertension, Aug. 2004, 13 pages.
Shigematsu, H. et al., "Randomized, Double-Blind, Placebo-Controlled Clinical Trial of Hepatocyte Growth Factor Plasmid for Critical Limb Ischemia," Gene Therapy, 2010, pp. 1152-1161, vol. 17.
Kibbe, M.R. et al., "Safety and Efficacy of Plasmid DNA Expressing Two Isoforms of Hepatocyte Growth Factor in Patients with Critical Limb Ischemia," Gene Therapy, 2016, pp. 306-312, vol. 23.
Henry, T.D. et al., "Safety of a Non-Viral Plasmid-Encoding Dual Isoforms of Hepatocyte Growth Factor in Critical Limb Ischemia Patients: A Phase I Study," Gene Therapy, 2011, pp. 788-794, vol. 18.
Deng, et al., "Secretory Expression of the Deleted Variant of Human Hepatocyte Growth Factor (hdHGF) in *Pichia pastoris*," *Chinese Journal of Biochemistry and Molecular Biology*, 2001, 17:590-594, China Academic Journal Electronic Publishing House, Beijing, China.
Kisselev, L., "Polypeptide Release Factors in Prokaryotes and Eukaryotes: Same Function, Different Structure," *Structure*, 2002, 10, pp. 8-9, Elsevier Science Ltd., Cambridge, Massachusetts, USA.
Liu, Y., "The human hepatocyte growth factor receptor gene: complete structural organization and promoter characterization," *Gene* 215:159-169, Elsevier/North-Holland (1998).
Miyazawa, K., et al., "Molecular Cloning and Sequence Analysis of cDNA for Human Hepatocyte Growth Factor," *Biochem. Biophys. Res. Commun. 163*:967-973, Academic Press (1989).
Nakamura, T., et al., "Molecular cloning and expression of human hepatocyte growth factor," *Nature 342*:440-443, Nature Publishing Group (1989).
NCBI Entrez, GenBank Database, Accession No. AC004960, "*Homo sapiens* PAC clone RP5-1098B1 from 7q11.23-q21, complete sequence," 51 pages (first available 1998).
Ngo et al., In The Protein Folding Problem and Tertiary Structure Prediction, 1994, Merz et al. (ed.), Birkhauser, Boston, MA, pp. 433 and 492-495.
Potrykus. Gene transfer to cereals: an assessment, Biotechnology, 1990, 8(6):535-542.
Rubin, et al., "A broad-spectrum human lung fibroblast-derived mitogen is a variant of hepatocyte growth factor," *Proc. Natl. Acad. Sci. USA*, 1991, 88:415-419, Proceedings of the National Academy of Sciences of the United States of America, 500 5th St., Washington, DC 20001.
Seki, T., et al., "Isolation and Expression of cDNA for Different Forms of Hepatocyte Growth Factor from Human Leukocyte," *Biochem. Biophys. Res. Commun. 172*:321-327, Academic Press (1990).
Seki, T., et al., "Organization of the human hepatocyte growth factor-encoding gene," *Gene* 102:213-219, Elsevier/North-Holland (1991).
Shima, N., et al., "Hepatocyte Growth Factor and its Variant with a Deletion of Five Amino Acids are Distinguishable in their Biological Activity and Tertiary Structure," *Biochem. Biophys. Res. Commun. 200*:808-815, Academic Press (1994).
Warnecke C. et al., "Efficient transcription of the human angiotensin II type 2 receptor gene requires intronic sequence elements," *Biochemical journal*, 1999, 340 (1), pp. 17-24, Portland Press, Colchester, Great Britain.
Wishart et al., "A Single Mutation Converts a Novel Phosphotyrosine Binding into a Dual-Specificity Phosphatase," *Journal of Biological Chemistry*, 1995, 270 (45), pp. 26782-26785, American Society for Biochemistry and Molecular Biology, Bethesda, MD, USA.
Witkowski et al., "Conversion of a A-Ketoacyl Synthase to a Malonyl Decarboxylase by Replacement of the Active-Site Cysteine with Glutamine," *Biochemistry*, 1999, 38 (36), pp. 11643-11650, American Chemical Society, Washington, DC, USA.
Office Action for Co-pending U.S. Appl. No. 10/944,277, mailed Jan. 9, 2008.
Office Action for Co-Pending U.S. Appl. No. 10/944,277, mailed Feb. 13, 2009.
Notice of Allowance and Fees Due for Co-Pending U.S. Appl. No. 10/944,277, mailed May 29, 2009.
Notice of Allowance and Fees Due for Co-Pending U.S. Appl. No. 10/944,277, mailed Oct. 23, 2009.
Office Action for Co-pending U.S. Appl. No. 11/957,170, mailed Jan. 28, 2010.

* cited by examiner

HYBRID HEPATOCYTE GROWTH FACTOR GENE HAVING HIGH EXPRESSION EFFICIENCY OF TWO HETEROTYPES OF HEPATOCYTE GROWTH FACTOR

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

[This application is a continuation] *The present application is a Reissue of U.S. Pat. No. 7,745,174, which issued on Jun. 29, 2010 from application Ser. No. 12/650,860, filed Dec. 31, 2009. U.S. application Ser. No. 12/650,860 is a divisional* of U.S. application Ser. No. 10/944,277, filed Sep. 20, 2004, *now U.S. Pat. No. 7,812,146,* which is a continuation of International Application No. PCT/KR03/00548, filed Mar. 20, 2003, which claims priority benefit to Korean Appl. No. 10-2002-0015074, filed Mar. 20, 2002, each of which [are] *is* herein incorporated by reference in [their] *its* entirety.

REFERENCE TO A SEQUENCE LISTING SUBMITTED ELECTRONICALLY

The content of the electronically submitted sequence listing ("sequencelisting.ascii.txt", 29,879 bytes, created on Dec. 30, 2009) filed with the application is incorporated herein by reference in its entirety.

BACKGROUND OF THE INVENTION

1. Field of the Invention

The present invention relates to a highly efficient hybrid Hepatocyte Growth Factor (HGF) gene which simultaneously expresses two heterotypes of HGF.

2. Related Art

The present invention relates to a hybrid HGF gene prepared by inserting an inherent or foreign intron between exons 4 and 5 in HGF cDNA, which has higher expression efficiency than HGF cDNA and simultaneously expresses two heterotypes of HGF and dHGF (deleted variant HGF).

HGF is a heparin binding glycoprotein called a scatter factor. A gene encoding HGF is located at chromosome [721.1] *7q21.1* and comprises 18 exons and 17 introns, having the nucleotide sequence of SEQ ID NO: 1 (Seki T., et al., Gene 102:213-219 (1991)). A transcript of about 6 kb is transcribed from the HGF gene, and then, a polypeptide HGF precursor consisting of 728 amino acids is synthesized therefrom. Simultaneously, a polypeptide of dHGF precursor consisting of 723 amino acids is also synthesized by an alternative splicing of the HGF gene. The biologically inactive precursors may be converted into active forms of disulfide-linked heterodimer by protease in serum. In the heterodimers, the alpha chain having a high molecular weight forms four kringle domains and an N-terminal hairpin loop like a preactivated peptide region of plasminogen. The kringle domains of a triple disulfide-bonded loop structure consisting of about 80 amino acids may play an important role in protein-protein interaction. The low molecular weight beta chain forms an inactive serine protease-like domain. dHGF consisting 723 amino acids is a polypeptide with deletion of five amino acids in the 1st kringle domain of the alpha chain, i.e., F, L, P, S and S.

It has been recently reported that both of HGF and dHGF have several biological functions, e.g., promoting the growth and morphogenesis of epithelial cell, melanocyte and endothelial cell. However, they are different in terms of immunological or biological properties.

For example, HGF shows about 20-fold, 10-fold and 2-fold higher activities than dHGF in promoting DNA synthesis in human umbilical cord venous endothelial cell, arterial smooth muscle cell and NSF-60 (murine myeloblast cell), respectively. dHGF shows about 3-fold and 2-fold higher activities than HGF in promoting DNA synthesis of LLC-PK1 (pig kidney epithelial cell), and OK (American opossum kidney epithelial cell) and mouse interstitial cell, respectively. HGF has a 70-fold higher solubility in PBS than dHGF. Several anti-dHGF monoclonal antibodies recognize only dHGF, but not HGF or a reduced form of dHGF, which implies structures of HGF and dHGF are different. Accordingly, the simultaneous synthesis of HGF and dHGF in vivo suggests that they biologically interact with each other (Shima, N. et al., Biochemical and Biophysical Research Communications 200:808-815 (1994)).

HGF secreted from mesoderm-derived cells has various biological functions, e.g., 1) inducing epithelial cells into a tubular structure; 2) stimulating vascularization from endothelial cells in vitro and in vivo; 3) regeneration of liver and kidney, owing to its anti-apoptosis activity; 4) organogenesis of kidney, ovary and testis; 5) controlling osteogenesis; 6) stimulating the growth and differentiation of erythroid hematopoietic precursor cells; and 7) axon sprouting of neurons (Stella, M. C. and Comoglio, P. M., The International Journal of Biochemistry & Cell Biology 31:1357-1362 (1999)). Based on these various functions, HGF or a gene encoding HGF may be developed as a therapeutic agent for treating ischemic or liver diseases. Actually, in vivo, the HGF may exist as either HGF or dHGF, and therefore, the coexpression of HGF and dHGF is important for maximizing the therapeutic effect. Accordingly, the present inventors have endeavored to develop a hybrid HGF gene which can simultaneously express HGF and dHGF with a high efficiency for gene therapy.

SUMMARY OF THE INVENTION

Accordingly, it is a primary object of the present invention to provide a hybrid HGF gene which simultaneously expresses two heterotypes of HGF.

In accordance with one aspect of the present invention, there is provide the hybrid HGF gene having an inherent or foreign intron is inserted between exons 4 and 5 of HGF cDNA.

It is a another object of the present invention to provide a recombinant vector comprising the hybrid HGF gene and a microorganism transformed with the above vector.

It is a still further object of the present invention to provide a pharmaceutical composition for treating or preventing ischemic or liver diseases, which comprises the HGF gene.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

Figure 1:
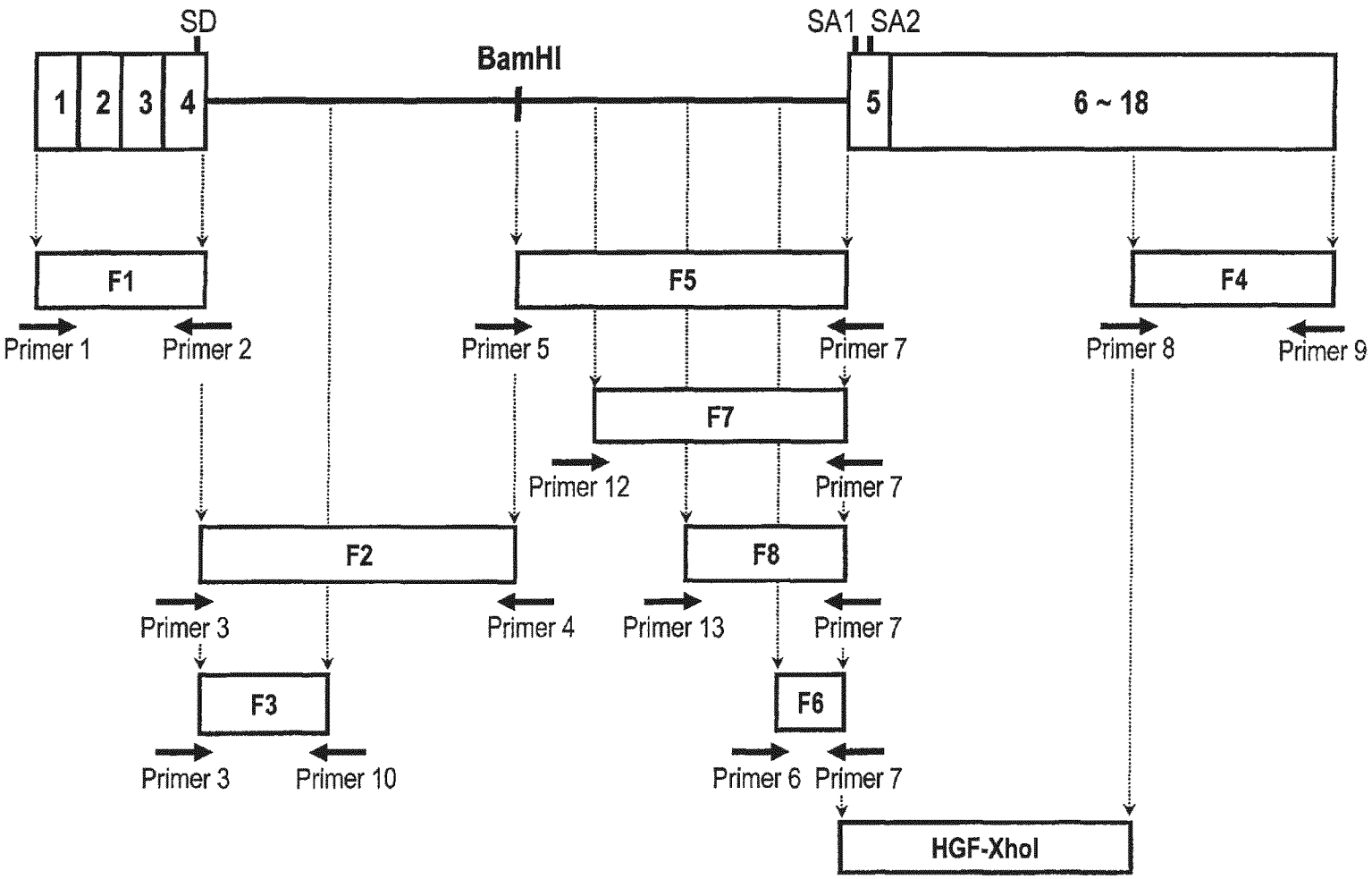
FIG. 1: a schematic diagram of HGF-X prototype illustrating the positions of the gene fragments.

The hybrid Hepatocyte Growth Factor (HGF) gene of the present invention comprises cDNA corresponding to the exons 1 to 18, and an inherent or foreign intron inserted between exons 4 and 5 of the cDNA. The intron comprises a fragment of the inherent intro or a recombinant sequence.

An embodiment of the hybrid HGF gene of the present invention comprising the inherent intron is 7113 bp long and has the nucleotide sequence of SEQ ID NO: 2. The hybrid HGF gene simultaneously expresses both HGF and dHGF, and has higher expression efficiency than HGF cDNA.

Codon degeneracy enables the hybrid HGF gene of the present invention to be modified or changed in the coding and/or non-coding region without altering the amino acid sequence of the protein and the expression of the gene. Accordingly, polynucleotides which is substantially identical to the hybrid HGF gene of SEQ ID NO:2, and the fragments thereof fall within the scope of the invention. "Substantially identical" means that the sequence homology is not less than 80%, preferably not less than 90%, and more preferably not less than 95%.

A hybrid HGF gene may comprise a fragment of inherent intron optionally having a small recombinant sequence inserted thereinto between exons 4 and 5 of HGF cDNA. Herein, such a hybrid HGF gene comprising a fragment of inherent intron designates "HGF-X". HGFX-6, HGF-X7 and HGF-X8 having the nucleotide sequence of SEQ ID Nos: 19 to 21, respectively, are preferred.

The hybrid HGF gene of the present invention is synthesized and inserted into an expression vector, according to the known genetic engineering methods. Then, the vector can be introduced into an appropriate host cells such as E. coli and yeast. For example, Escherichia coli Top10F' may be transfected with HGF-X7 gene of the present invention. Escherichia coli Top10F' pCK-HGFX7 and Escherichia coli Top10F' pCP-HGFX7 then obtained were deposited as the accession numbers KCCM-10361 and KCCM-10362, respectively, on Mar. 12, 2002.

By using the transformed cells, the gene of the present invention and the protein encoded thereby may be produced on a large scale.

The vector of the present invention may selectively comprise sequence(s) for regulating gene expression such as promoter or terminator, self-replication sequence and secretory signal, depending on host cells.

Further, the present invention comprises a pharmaceutical composition for treating or preventing ischemic and liver diseases, which comprises the hybrid HGF gene or the vector comprising the gene as an active ingredient. Preferably, the composition is formulated for injection.

The composition of the present invention may further comprise pharmaceutically acceptable carriers. Any of the conventional procedures in the pharmaceutical field may be used to prepare oral formulations such as tablets, capsules, pills, granules, suspensions and solutions; rejection formulations such as solutions, suspensions, or dried powders that may be mixed with distilled water before injection; locally-applicable formulations such as ointments, creams and lotions; and other formulations.

Carriers generally used in the pharmaceutical field may be employed in the composition of the present invention. For example, orally-administered formulations may include binders, emulsifiers, disintegrating agents, excipients, solubilizing agents, dispersing agents, stabilizing agents, suspending agents, coloring agents or spicery. Injection formulations may comprise preservatives, unagonizing agents, solubilizing agents or stabilizing agents. Preparation for local administration may contain bases, excipients, lubricants or preservatives. Any of the suitable formulations known in the art (Remington's Pharmaceutical Science [the new edition], Mack Publishing Company, Eaton Pa.) may be used in the present invention.

The inventive composition can be clinically administered as various oral and parenteral formulations. A suitable formulation may be prepared using such excipients as additives, enhancers, binders, wetting agents, disintegrating agents and surfactants, or diluents. Solid formulations for oral administration include pills, tablets, dusting powder, granules and capsules. Those solid formulations may be prepared by mixing one or more excipients, e.g. starch, calcium carbonate, sucrose, lactose and gelatin with dibenzylbuthyllacton lignan derivatives. Also, lubricants such as magnesium stearate and talc may be included in the present formulation. Liquid formulations for oral administration include suspension, solution, emulsion and syrup. Those formulations may contain wetting agents, sweeteners, aromatics and preservatives, in addition to general simple diluents such as water and liquid paraffin. Formulations for parenteral administration include sterilized aqueous solution, suspension, emulsion, freeze-dried alternative treatment and suppositories. Water-insoluble excipients and suspending agents comprise vegetable fats such as propylene glycol, polyethylene glycol and olive oil, and injectable esters such as ethyl oleate. Witepsol®, Macrogol®, Tween® 61, cacao fats, laurin fats and glycerogelatins may be used as bases of suppositories.

The inventive composition may be administered orally or via parenteral routes such as intravenous, intramuscular, subcutaneous, intraabdominal, sternal and arterial injection or infusion, or topically through rectal, intranasal, inhalational or intraocular administration.

It should be understood that the typical daily dose of composition of the present invention ought to be determined in light of various relevant factors including the conditions to be treated, the chosen route of administration, the age, sex and body weight of the individual patient, and the severity of the patient's symptom, and can be administrated in a single dose or in divided dose. Therefore, the daily dose should not be construed as a limitation to the scope of the invention in any way.

The following Examples are given for the purpose of illustration only, and are not intended to limit the scope of the invention.

EXAMPLE 1

Preparation of Hybrid Gene Constructs Encoding Human HGF (1) Cloning of HGF Gene Fragments Obtained from Genomic DNA Human HepG2 cells (ATCC Accession NO: HB-8065) were suspended in TES buffer (10 mM Tris-HCl; 1 mM EDTA; 0.7% SDS) and treated with 400 μg/Ml of proteinase K at 50° C. for 1 hour. Subsequently, genomic DNA was extracted from the cell suspension by phenol/chloroform extraction and ethanol precipitation according to the conventional method in the art.

In the PCR amplification, the extracted genomic DNA was employed as a template DNA. As primer pairs, the synthetic nucleotides of SEQ ID NOs: 3 and 4 were employed to obtain DNA fragments containing: HGF gene fragment 2 (HGF-F2), SEQ ID NOs: 3 and 5; HGF-F3, SEQ ID NOs: 6 and 7; HGF-F5, SEQ ID NOs: 8 and 7; HGF-F7, SEQ ID NOs: 9 and 7; HGF-F8, SEQ ID NOs: 10 and 7; HGF-F6, respectively (FIG. 1). The PCR amplification mixture was prepared by mixing 1 μl of template DNA, 1 μl each of primer (10 pmol/μl), 10 μl of dNTP (10 mM), 3.5 unit of Expand High Fidelity enzyme (Gibco BRL, USA) and 10 μl of enzyme buffer solution and adjusted to a final volume of 100 μl with distilled water. 30 cycles of the PCR amplification was carried out, each cycle consisting of 1 min at 94° C., 1 min at 55° C. and 30 sec at 72° C. The primers used herein and the amplified gene fragments obtained therefrom are shown in Table 1.

TABLE 1

| 5' primer | 3' primer | Amplified fragment |
|---|---|---|
| gHGF3 (SEQ ID NO: 3) | gHGF4 (SEQ ID NO: 4) | HGF gene fragment 2 (HGF-F2) |
| gHGF3 (SEQ ID NO: 3) | gHGF10 (SEQ ID NO: 5) | HGF gene fragment 3 (HGF-F3) |
| gHGF5 (SEQ ID NO: 6) | gHGF7 (SEQ ID NO: 7) | HGF gene fragment 5 (HGF-F5) |
| gHGF12 (SEQ ID NO: 8) | gHGF7 (SEQ ID NO: 7) | HGF gene fragment 7 (HGF-F7) |
| gHGF13 (SEQ ID NO: 9) | gHGF7 (SEQ ID NO: 7) | HGF gene fragment 8 (HGF-F8) |
| gHGF6 (SEQ ID NO: 10) | gHGF7 (SEQ ID NO: 7) | HGF gene fragment 6 (HGF-F6) |

The amplified HGF-F2 comprised the sequence ranging from 392 to 2247 of human HGF cDNA prototype (HGF-X1; composed of exons 1 to 4-intron 4-exons 5 to 18) of SEQ ID NO: 2; HGF-F3, the sequence ranging from 392 to 727; HGF-5, the sequence ranging from 2229 to 5471; HGF-F6, the sequence ranging from 5117 to 5471; HGF-F7, the sequence ranging from 3168 to 5471; and HGF-F8, the sequence ranging from 4168 to 5471.

Figure 2:
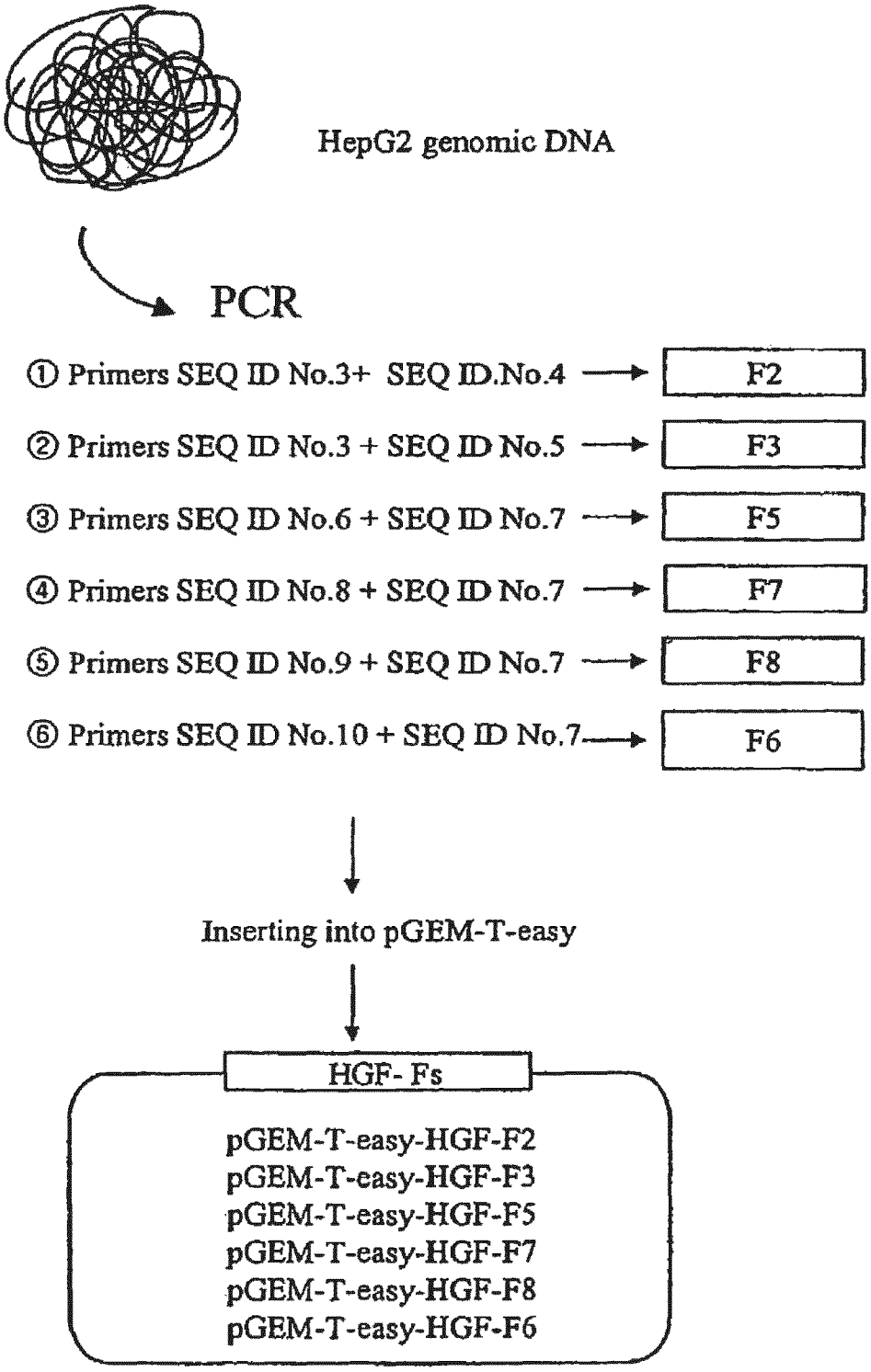
FIG. 2: a process for cloning gene fragments from HepG2 genomic DNA.

The amplified HGF gene fragments were each inserted into the multiple cloning site of pGEM-T easy vector (Promega, WI, USA) to obtain pGEM-T easy-HGF-F2, pGEM-T easy-HGF-F3, pGEM-T easy-HGF-F5, pGEM-T easy-HGF-F6, pGEM-T easy-HGF-F7 and pGEM-T easy-HGF-F8, respectively (FIG. 2). The nucleotide sequences of the amplified HGF gene fragments were confirmed by a sequence analysis.

(2) Cloning of HGF Gene Fragments Obtained from cDNA

In the PCR amplification, human placenta cDNA (Clontech, CA, USA) was employed as a template DNA under the same condition as described in Example 1. As primer pairs, the synthetic oligonucleotides of SEQ ID NOs: 11 and 12, and SEQ ID NOs: 13 and 14 were employed to obtain DNA fragments containing HGF-F1 and HGF-F4, respectively. Further, DNA fragments containing cDNAs of HGF gene (cHGF) and deleted HGF gene (dHGF) were amplified by PCR using synthetic oligonucleotides of SEQ ID NOs: 15 and 16 as a primer pair, respectively. dHGF is a HGF gene with deletion of 5 base sequences.

The primers used herein and the amplified gene fragments obtained therefrom are shown in Table 2.

TABLE 2

| 5' primer | 3' primer | Amplified fragment |
|---|---|---|
| gHGF1 (SEQ ID NO: 11) | gHGF2 (SEQ ID NO: 12) | HGF gene fragment 1 (HGF-F1) |
| gHGF8 (SEQ ID NO: 13) | gHGF9 (SEQ ID NO: 14) | HGF gene fragment 4 (HGF-F4) |
| cHGF5 (SEQ ID NO: 15) | cHGF3 (SEQ ID NO: 16) | HGF gene cDNA (cHGF) |
| | | dHGF gene cDNA (dHGF) |

The amplified HGF-F1 and HGF-F4 comprised the nucleotide sequences ranging from 1 to 402 and from 6533 to 7113 of SEQ ID NO: 2 of human HGF cDNA prototype, respectively. HGF gene cDNA comprised the nucleotide sequence ranging from 1 to 2184 of SEQ ID NO: 1 of human HGF gene, and dHGF gene cDNA has the same sequence as HGF gene cDNA except for the deletion of the sequence ranging from 483 to 495.

Figure 3:
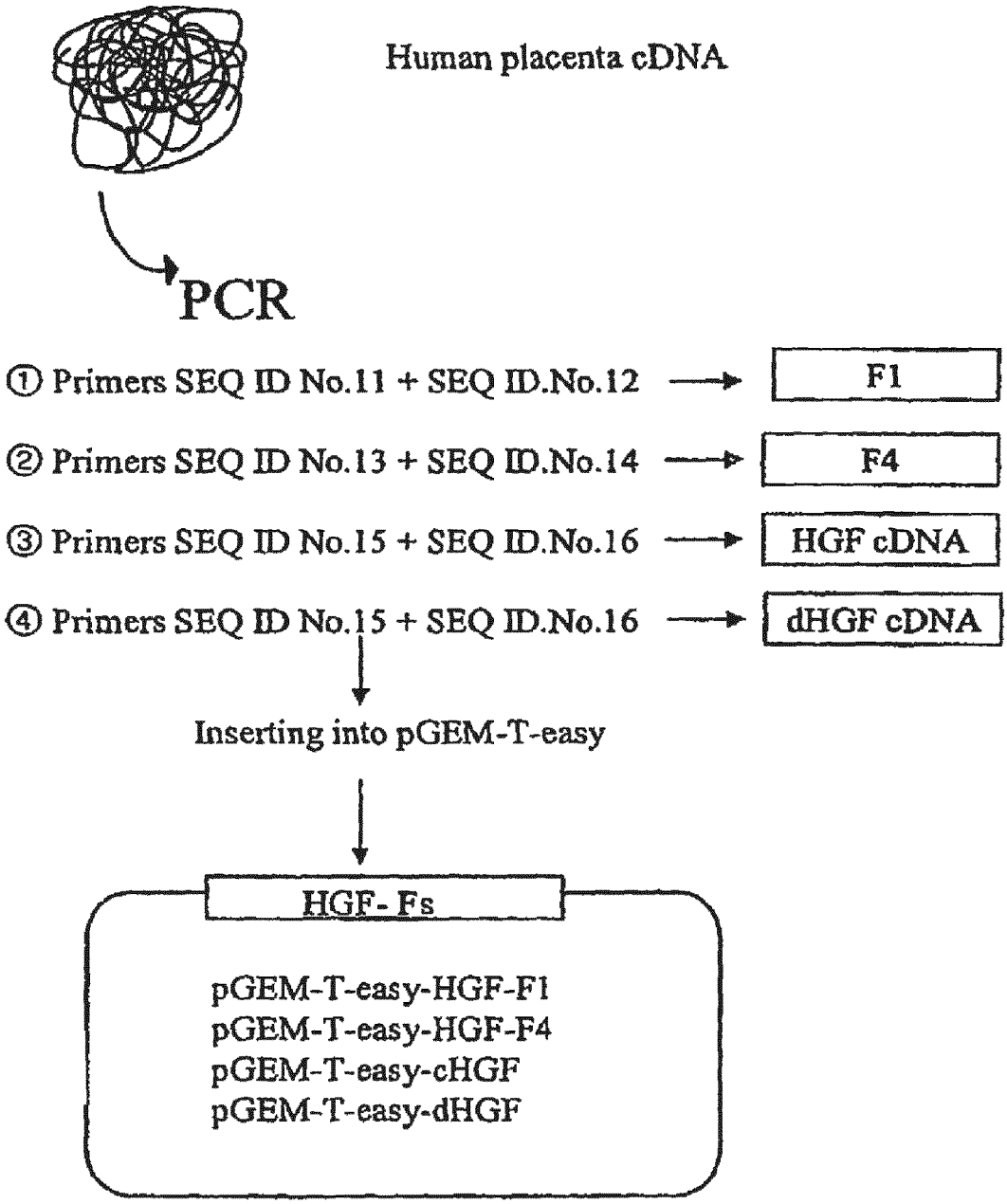
FIG. 3: a process for cloning gene fragments from human placenta cDNA.

The amplified fragments of HGF gene were each inserted into the multiple cloning site of pGEM-T easy vector (Promega, WI, USA) to obtain pGEM-T easy-HGF-F1, pGEM-T easy-HGF-F4, pGEM-T easy-cHGF and pGEM-T easy-dHGF, respectively (FIG. 3). The nucleotide sequences of the human HGF gene fragments, HGF gene cDNA and dHGF gene cDNA were confirmed by sequence analyses.

(3) Preparation of Hybrid HGF Gene Constructs

Figure 4A:
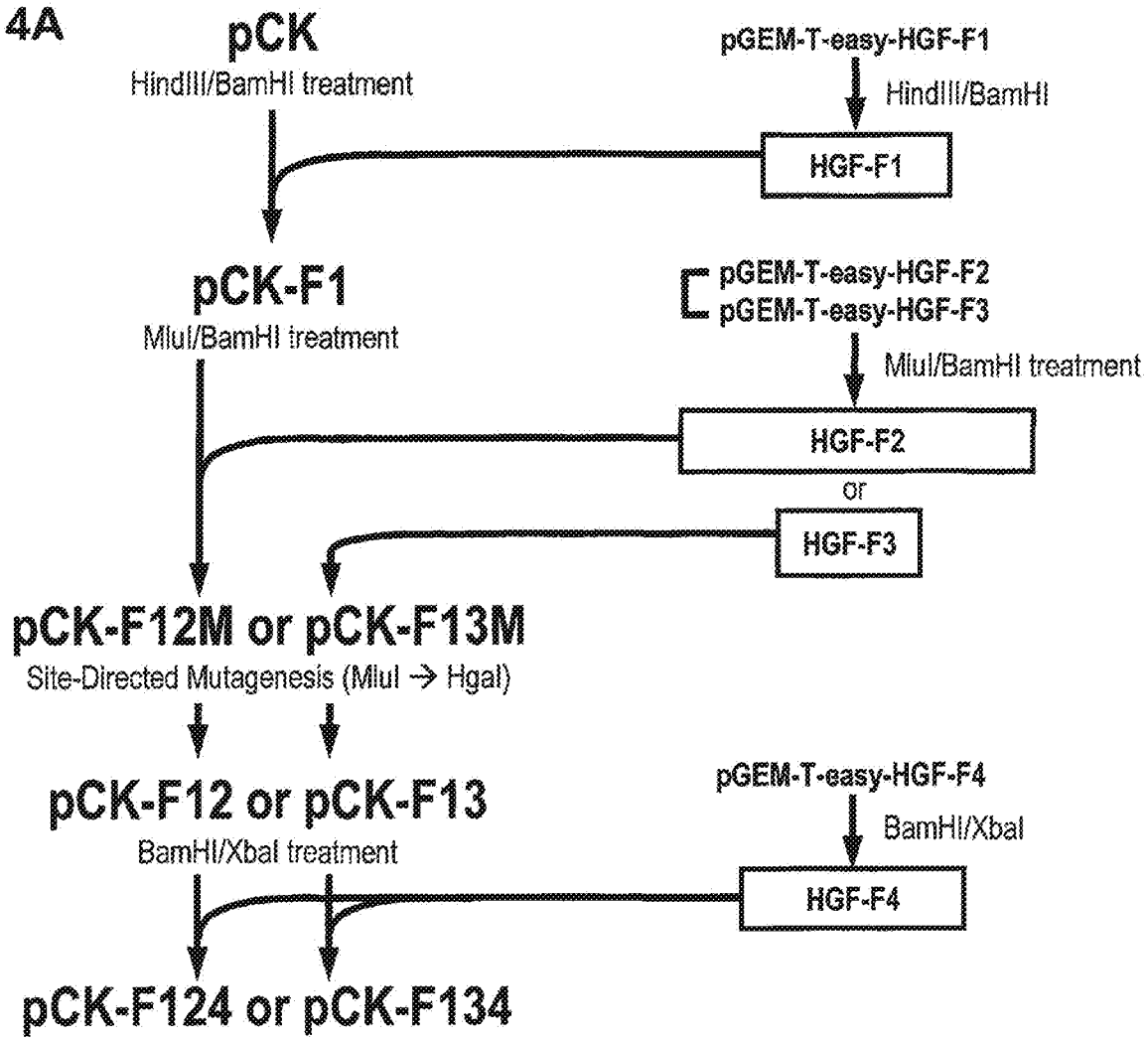
FIGS. 4A and 4B: processes for preparing expression vectors pCK-HGF-X.
Figure 4B:
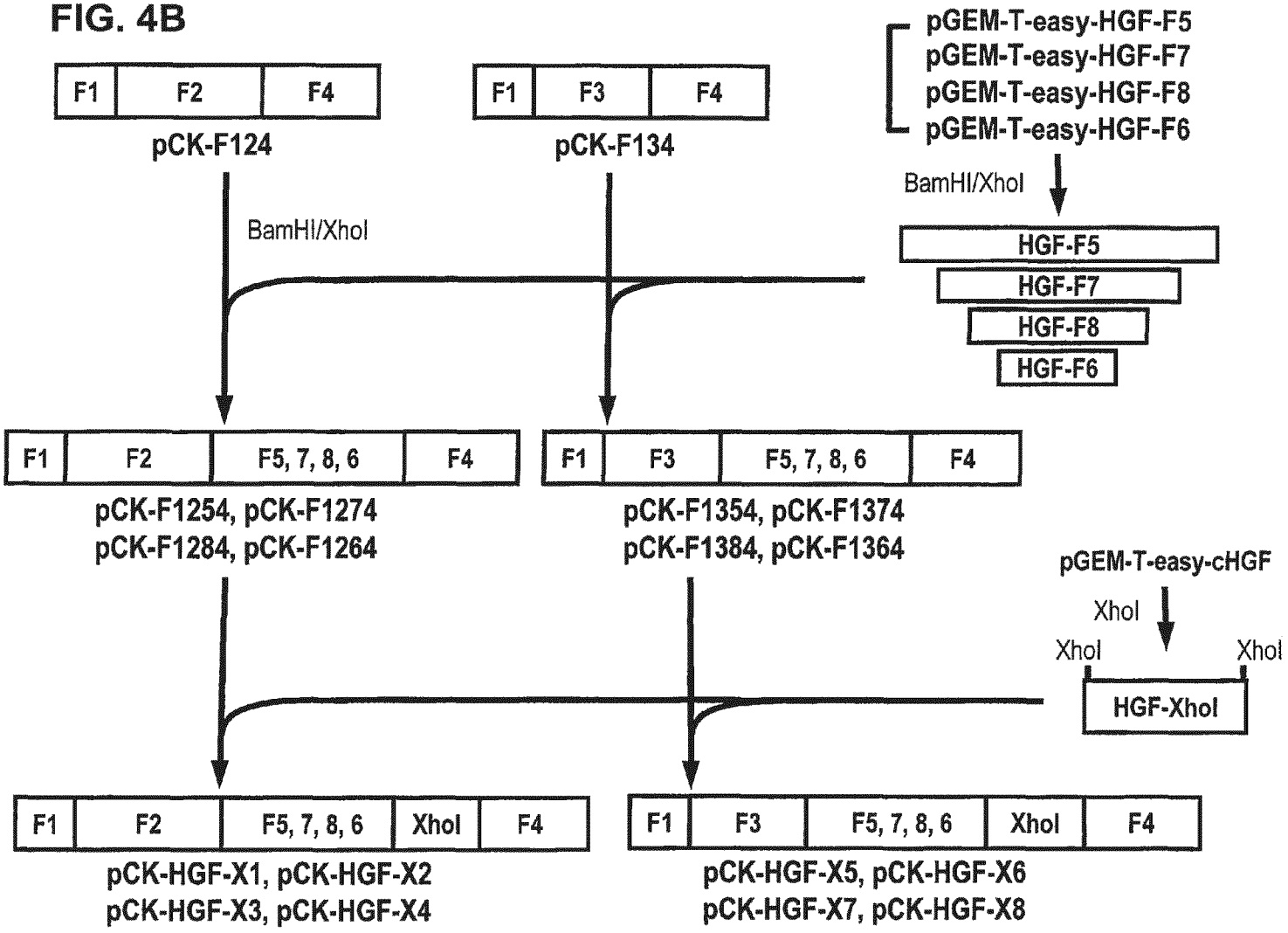

Hybrid HGF gene constructs of genomic DNA and cDNA were prepared by combining the fragments of HGF gene cloned in steps (1) and (2) as follows (FIGS. 4A and 4B).

Plasmid pGEM-T-easy-HGF-F1 was treated with HindIII/BamHI to obtain HGF-F1. Plasmid pCK (see PCT International Publication NO: WO/0040737) was treated with HindIII/BamHI, and HGF-F1 was inserted thereinto to obtain pCK-F1. And then, plasmids pGEM-T-easy-HGF-F2 and pGEM-T-easy-HGF-F3 were treated with MluI/BamHI to obtain HGF-F2 and HGF-F3, respectively. pCK-1 was treated with MluI/BamHI, and then HGF-F2 and HGF-F3 were inserted thereinto to obtain pCK-F12M and pCKF13M. The MluI restriction site of vectors pCK-F12M and pCK-F13M was substituted with an HgaI restriction site by employing a site-directed mutagenesis kit (Stratagene, CA., USA) to obtain pCK-F12 and pCK-F13, respectively.

Further, plasmid pGEM-T-easy-HGF-F4 was treated with BamHI/XbaI to obtain HGF-F4. pCK-F12 and pCK-F13 were treated with BamHI/XbaI, and HGF-F4 was inserted thereinto to obtain pCK-F124 and pCK-F134, respectively. And then, plasmids pGEM-T-easy-HGF-F5, pGEM-T-easy-HGF-F6, pGEM-T-easy-HGF-F7 and pGEM-T-easy-HGF-F8 were treated with BamHI/XhoI to obtain HGF-F5, HGF-F6, HGF-F7 and HGF-F8, respectively. pCK-F124 and pCK-F134 were treated with BamHI/XhoI, and then HGF-F5, HGF-F6, HGF-F7 and HGF-F8 were inserted thereinto to obtain pCK-F1254 and pCK-F1264, pCK-F1274, pCK-F1284, pCK-F1354, pCK-F1364, pCK-F1374 and pCK-F1384, respectively.

Figure 5:
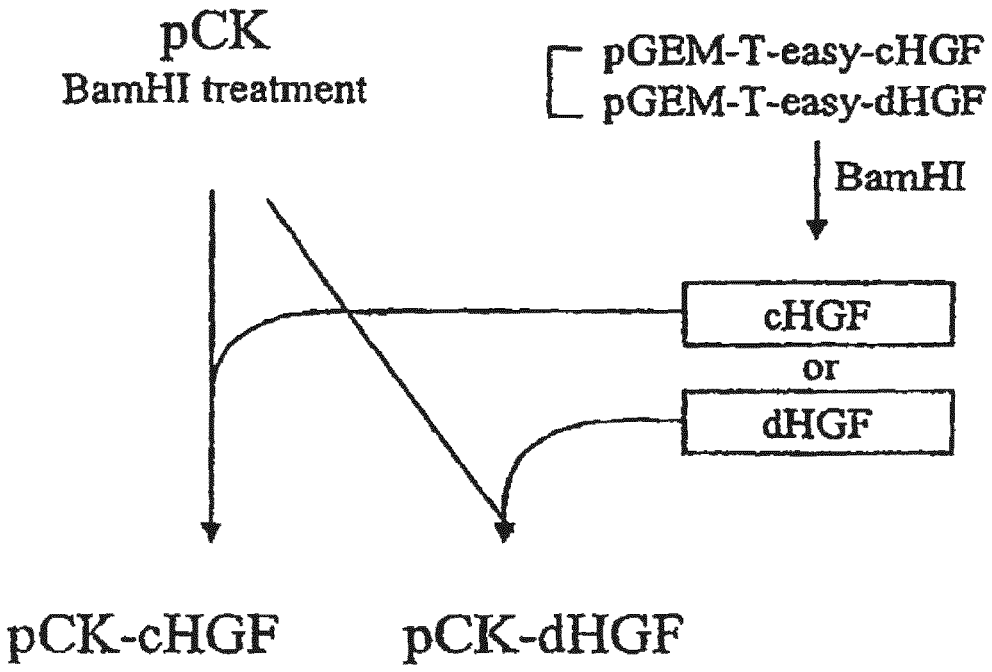
FIG. 5: a process for preparing expression vectors pCK-cHGF and pCK-dHGF.

And then, pGEM-T easy-cHGF was treated with XhoI to obtain cDNA fragment of HGF gene (HGF-XhoI) of about 1100 bp. Then, HGF-XhoI was inserted into pCK-F1254, pCK-F1264, pCK-F1274, pCK-F1284, pCK-F1354, pCK-F1364, pCK-F1374 and pCK-F1384 to obtain pCK-HGF-X1, pCK-HGF-X2, pCK-HGF-X3, pCK-HGF-X4, pCK-HGF-X5, pCK-HGF-X6, pCK-HGF-X7 and pCK-HGF-X8, respectively. On the other hand, pGEM-T easy-cHGF and pGEM-T easy-dHGF were treated with BamHI to obtain HGF gene cDNA and dHGF gene cDNA. Then, HGF gene cDNA and dHGF gene cDNA were inserted into the BamHI restriction site of pCK to obtain pCK-cHGF and pCK-dHGF, respectively (FIG. 5).

(4) Preparation of an Expression Vector Containing a Hybrid HGF Gene Construct

Figure 6:
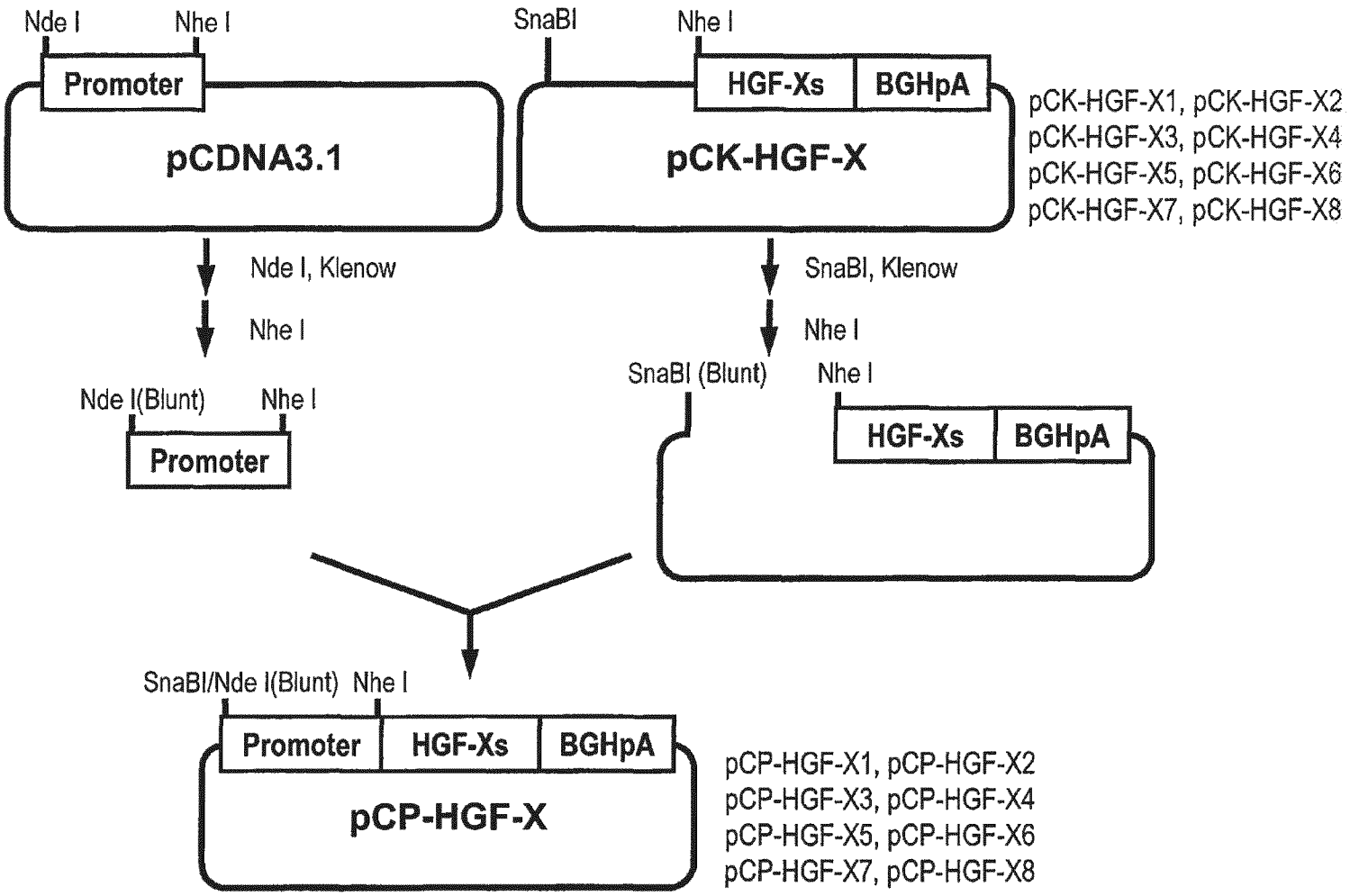
FIG. 6: a process for preparing expression vectors pCP-HGF-X family.

Plasmid pcDNA3.1 (Invitrogen, USA) was digested with NdeI, treated with the Klenow fragment to build blunt ends, and then digested with NheI to obtain a DNA fragment containing human cytomegalovirus promoter. Plasmids pCK-HGF-X1, pCK-HGF-X2, pCK-HGF-X3, pCK-HGF-X4, pCK-HGF-X5, pCK-HGF-X6, pCK-HGF-X7 and pCK-HGF-X8 were digested with SnaBI, treated with the Klenow fragment to make blunt ends and digested with NheI, and then the above DNA fragment containing human cytomegalovirus promoter was inserted thereinto to obtain pCP-HGF-X1, pCP-HGF-X2, pCP-HGF-X3, pCP-HGF-X4, pCP-HGF-X5, pCP-HGF-X6, pCP-HGF-X7 and pCP-HGF-X8, respectively (FIG. 6).

Figure 7:
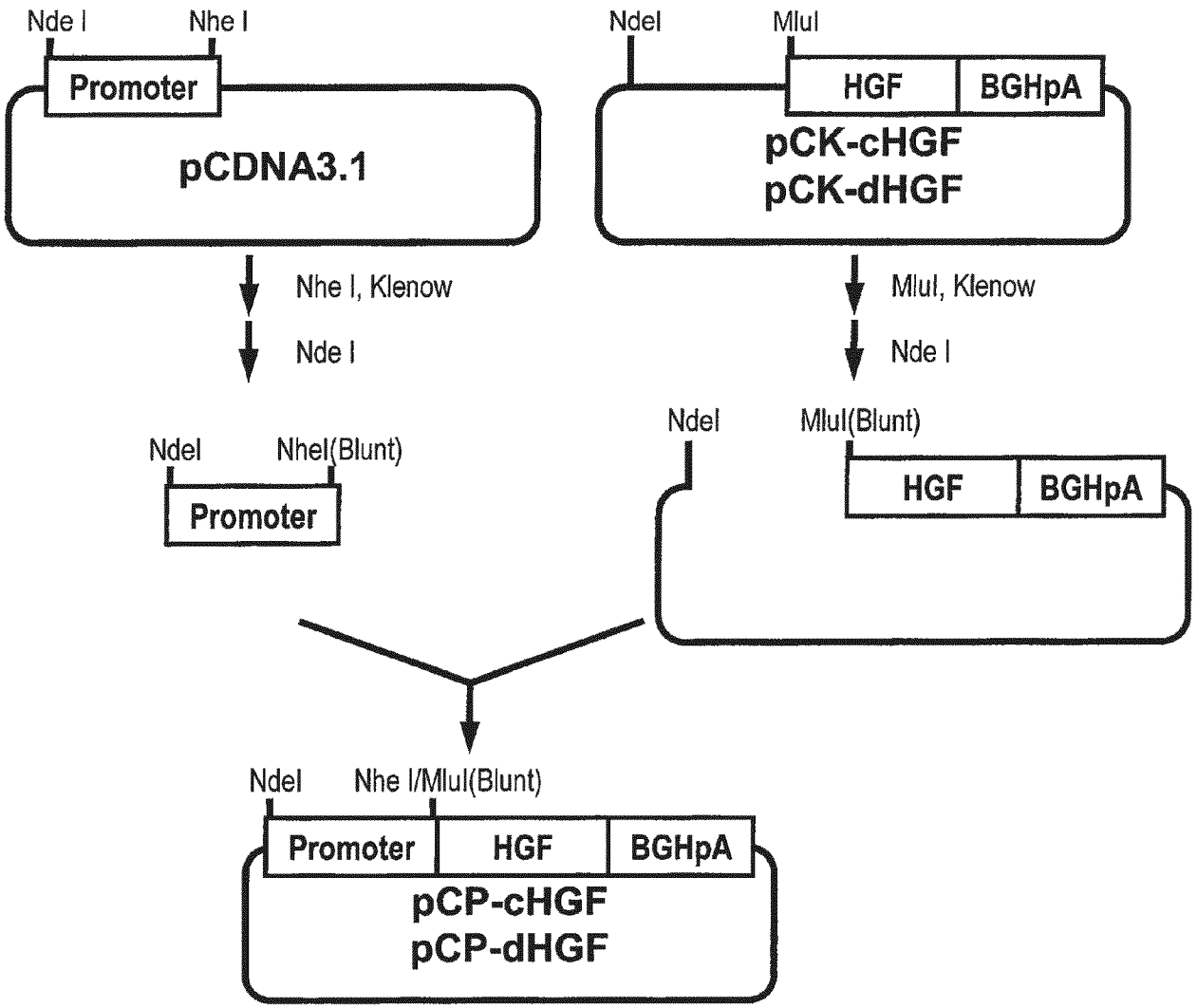
FIG. 7: a process for preparing expression vectors pCP-cHGF and pCP-dHGF.

Plasmid pcDNA3.1 (Invitrogen, USA) was digested with NheI, treated with the Klenow fragment to make blunt ends and digested with NdeI to obtain the DNA fragment containing human cytomegalovirus promoter. pCK-cHGF and pCK-dHGF were digested with MluI, treated with the Klenow fragment to make blunt ends and digested with NdeI, and then the above DNA fragment containing human cytomegalovirus promoter was inserted thereinto to obtain pCP-cHGF and pCP-dHGF, respectively (FIG. 7).

EXAMPLE 2

Examination of the Expression Efficiency of Hybrid HGF Gene Construct and the Coexpression of HGF/dHGF Studies was conducted to examine whether the hybrid HGF gene constructs (HGF-X1 to HGF-X8) obtained in Example 1 can simultaneously express HGF and dHGF and whether there is any difference in the gene expression level between hybrid HGF gene constructs and HGF cDNA.

(1) Gene Expression Efficiency

First, 5 μg of pCP-HGF-X2, pCP-HGF-X3, pCP-HGF-X6, pCP-HGF-X7 and pCP-HGF-X8 were transfected into $5\times10^6$ cells of 293 cell (ATCC CRL 1573) together with 0.5 μg of DONAI-LacZ (TAKARA SHUZO, Japan) DNA using FuGENE6 (Gibco BRL, MD, USA), according to the manufacturer's instructions. At this time, 5 μg each of pCP-cHGF and pCP-dHGF were used as controls, and DONAI-LacZ DNA was used to calibrate the infection efficiency. 3 hours after transfection, cells were re-fed with a fresh medium and further cultured for 48 hours. The culture solution thus obtained was divided into two parts. One part of the 293 cell culture solution was subjected to RNA extraction, and the other, to measurement of LacZ activity. The LacZ activity was measured using an activity measuring kit (Stratagene, CA, USA) according to the manufacturer's instructions.

Figure 8:
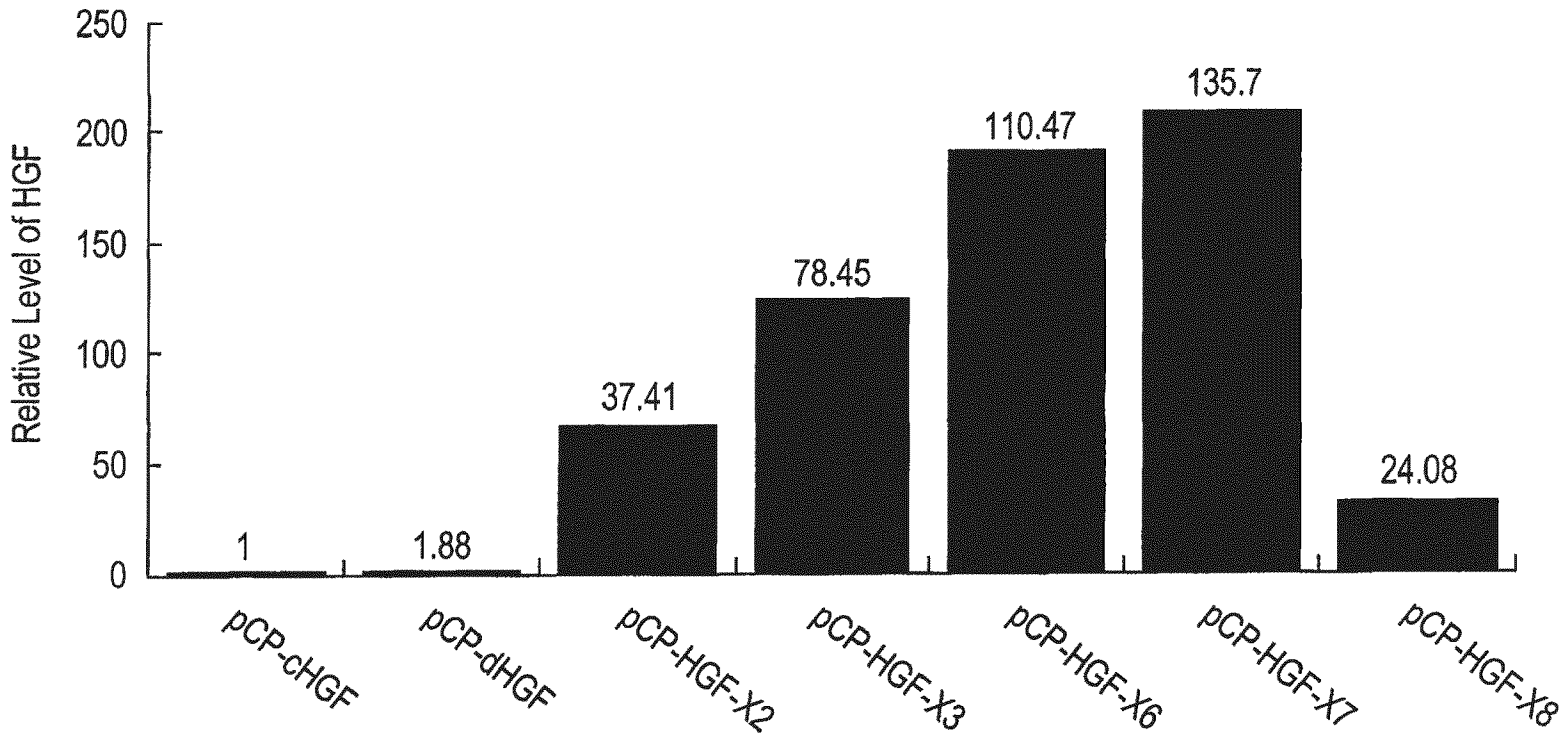
FIG. 8: gene expression levels of pCP-cHGF, pCP-dHGF and pCP-HGF-X.

In order to compare the gene expression levels, the amount of HGF in the cell culture was measured by an enzyme-linked immunosorbent assay kit (ELISA, R&D System, MN, USA). After calibrating the infection efficiency by the measured LacZ activity, the expression level of HGF-X gene was found to be from 20 to 150-fold higher than those of HGF cDNA and dHGF cDNA (FIG. 8). HGF-X7, in particular, showed the highest gene expression level.

(2) Coexpression of HGF and dHGF

In order to examine coexpression of HGF and dHGF from hybrid HGF gene constructs, total cellular RNAs were extracted from the transfected 293 cells using the Trizol method (Trizol; Gibco BRL, USA) and subjected to RT-PCR to obtain cDNA. Then, using cDNA as a template DNA, PCR amplification was carried out using synthetic oligonucleotides of SEQ ID NOs: 17 and 18 as a primer pair. The PCR amplification mixture was prepared by mixing 1 μl of the template DNA, 1 μl each of the primer (10 pmol/μl), 10 μl of dNTP (10 mM), 3.5 unit of Taq polymerase (TAKARA SHUZO, Japan) and 10 μl of enzyme buffer solution and adjusted to a final volume of 100 μl with distilled water. 30 cycles of PCR amplification was conducted, each cycle consisting of 1 min at 94° C., 1 min at 55° C., and 90 sec at 72° C.

The amplified PCR products corresponded to the boundary region between exons 4 and 5 of HGF gene; HGF gene cDNA of 142 by and dHGF gene cDNA of 127 bp, respectively. With no splicing, the PCR product of at least 1 kb in length was amplified; and if alternative splicing occurred, HGF gene cDNA of 142 bp and dHGF gene cDNA of 127 by were simultaneously synthesized and amplified. The amplified PCR products were distinguished by electrophoresis on a 12% polyacrylamide gel.

Figure 9:
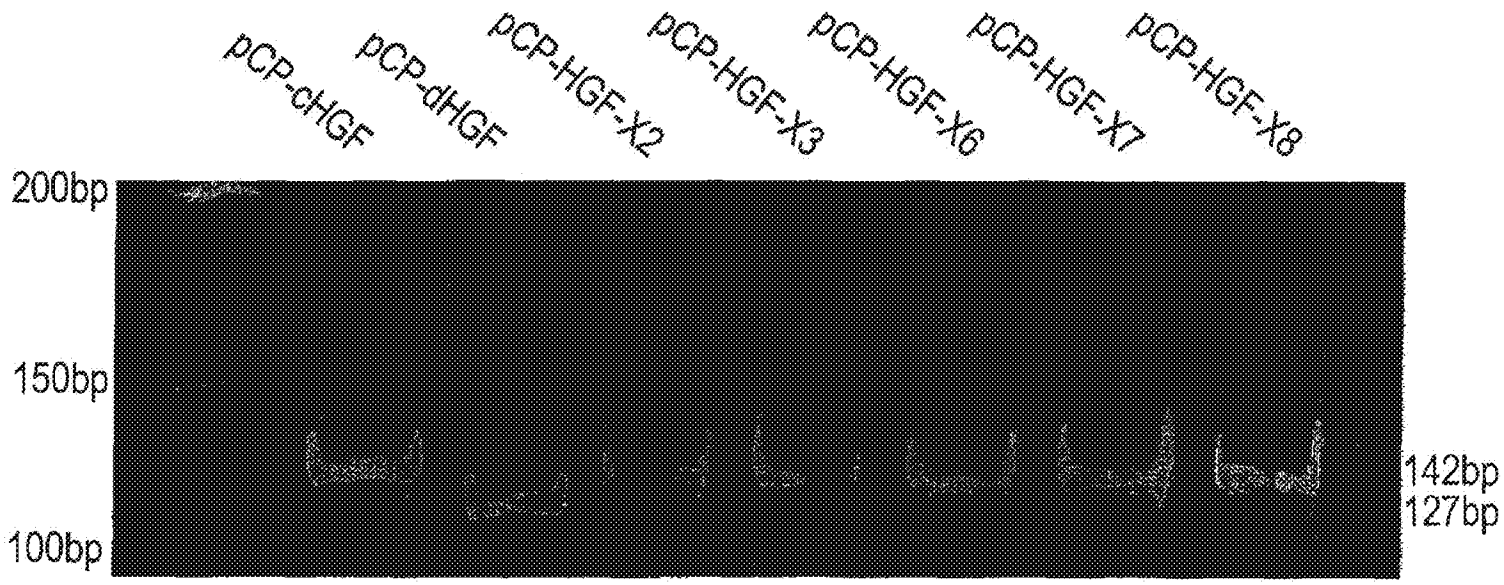
FIG. 9: gene expression patterns of pCP-cHGF, pCP-dHGF and pCP-HGF-X observed by electrophoresis on 12% polyacrylamide gel.

As shown in FIG. 9, while the bands of 142 by and 127 by were detected in the lanes loading HGF gene cDNA and dHGF gene cDNA, respectively, both bands of 142 by and 127 by were detected in the lanes loading HGF-X. The above results suggest that HGF and dHGF are simultaneously expressed from hybrid HGF-X gene constructs of the present invention.

EXAMPLE 3

Comparison of Expression Levels of HGF-X7, HGF Gene cDNA and dHGF Gene cDNA (In Vivo)

100 μg each of pCP-HGF-X7, pCP-cHGF and pCP-dHGF were injected into the [enterior] *anterior* tibial muscle of the hind limb of mice with an insulin syringe. After 5 days, the mice were sacrificed and the muscles around the injection spot were removed and smashed in a protein extraction buffer (25 mM Tris-HCl (pH 7.4), 50 mM NaCl, 0.5% Na-deoxycholate, 2% NP-40, 0.2% SDS) to separate total proteins. The amount of the total proteins was measured with a DC protein analysis kit (Bio-Rad Laboratories, CA, USA) and the amount of expressed HGF was determined with an ELISA kit (R&D System) according to the manufacturer's instruction.

Figure 10:
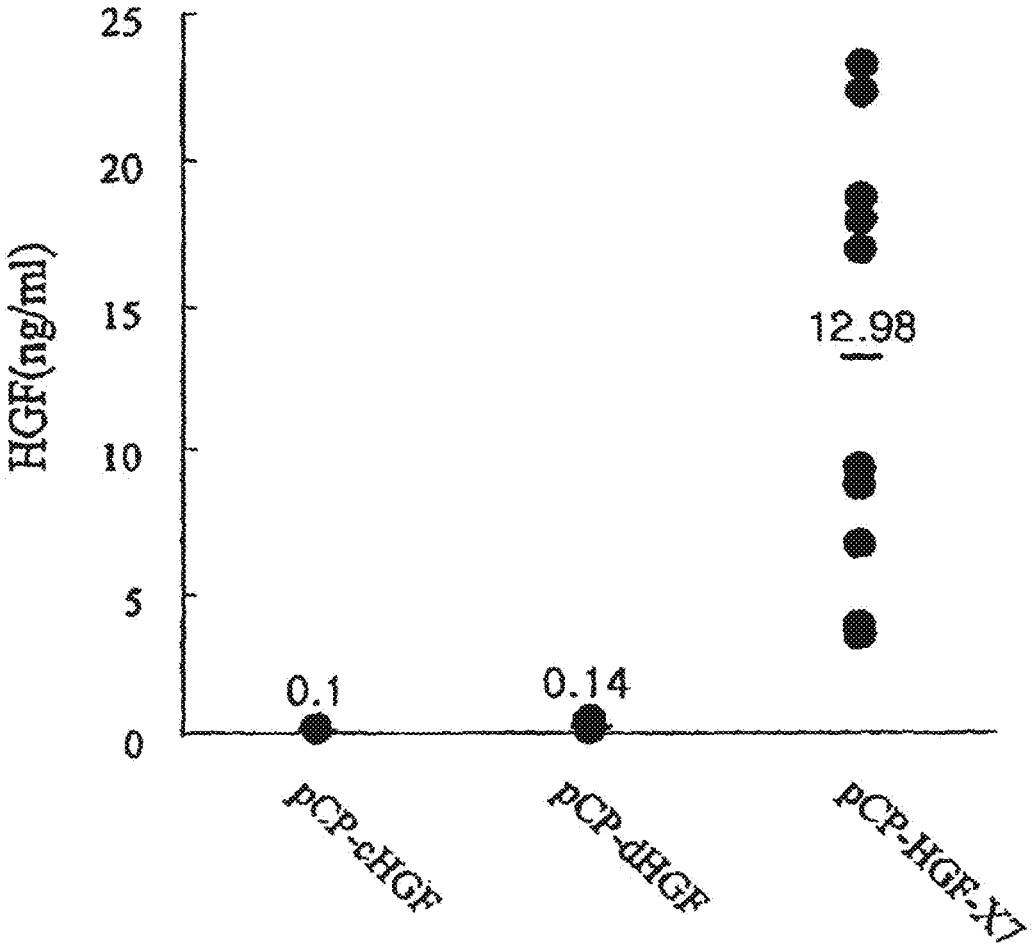
FIG. 10: gene expression levels of pCP-cHGF, pCP-dHGF and pCP-HGF-X7, in vivo.

As can be seen from the result shown in FIG. 10, the amount of HGF expressed from HGF-X7 is 250-fold higher than that from HGF gene cDNA or dHGF gene cDNA.

Together with the result of the experiment of Example 2 (in vivo), this result demonstrates that the expression efficiency of HGF-X gene is much superior to those of HGF gene cDNA or dHGF gene cDNA.

EXAMPLE 4

Gene Therapy Employing HGF-X7 in a Rabbit Ischemic Hind Limb Model

In order to examine whether HGF-X7 gene is effective in the treatment of ischemic hind limb disease, gene therapy was carried out on a rabbit ischemic hind limb model as follows.

A rabbit ischemic hind limb model, which is a standard animal model for the ischemic limb disease, was prepared by the method described by Takeshita et al., Journal of Clinical Investigation 93:662 (1994). At the day before operation (day 0), each of 30 white rabbits from New Zealand (male, from 3.8 to 4.2 kg) was intramuscularly injected with 5 mg/kg of xylazine and, then, anesthetized by an intramuscular injection of 50 mg/kg of ketamine. Subsequently, the left femoral region of the rabbit was incised and all branches of the femoral artery were separated and tied. The region from the proximal part to the branching point of the saphenous and popliteal arteries was incised to prepare the model. After the operation, 15 mg/kg/day of cefazolin was injected intramuscularly for 5 days and 0.3 mg/day of morphine, for 10 days. 10 days after the operation (day 10), angiography was carried out for the left hind limb where the ischemia was induced, and the degree of arteriogenesis was recorded as a basal level. The rabbits were randomly divided into two groups and injected at four sites in the femoral muscle with 500 μg of plasmid pCP-HGF-X7 (experimental group) or 500 μg of plasmid pCP (control), respectively. 40 days after the operation (day 40), angiography was carried out again for the left hind limb and the degree of arteriogenesis at the arteriole level was determined and compared to that of day 10.

Figure 11:
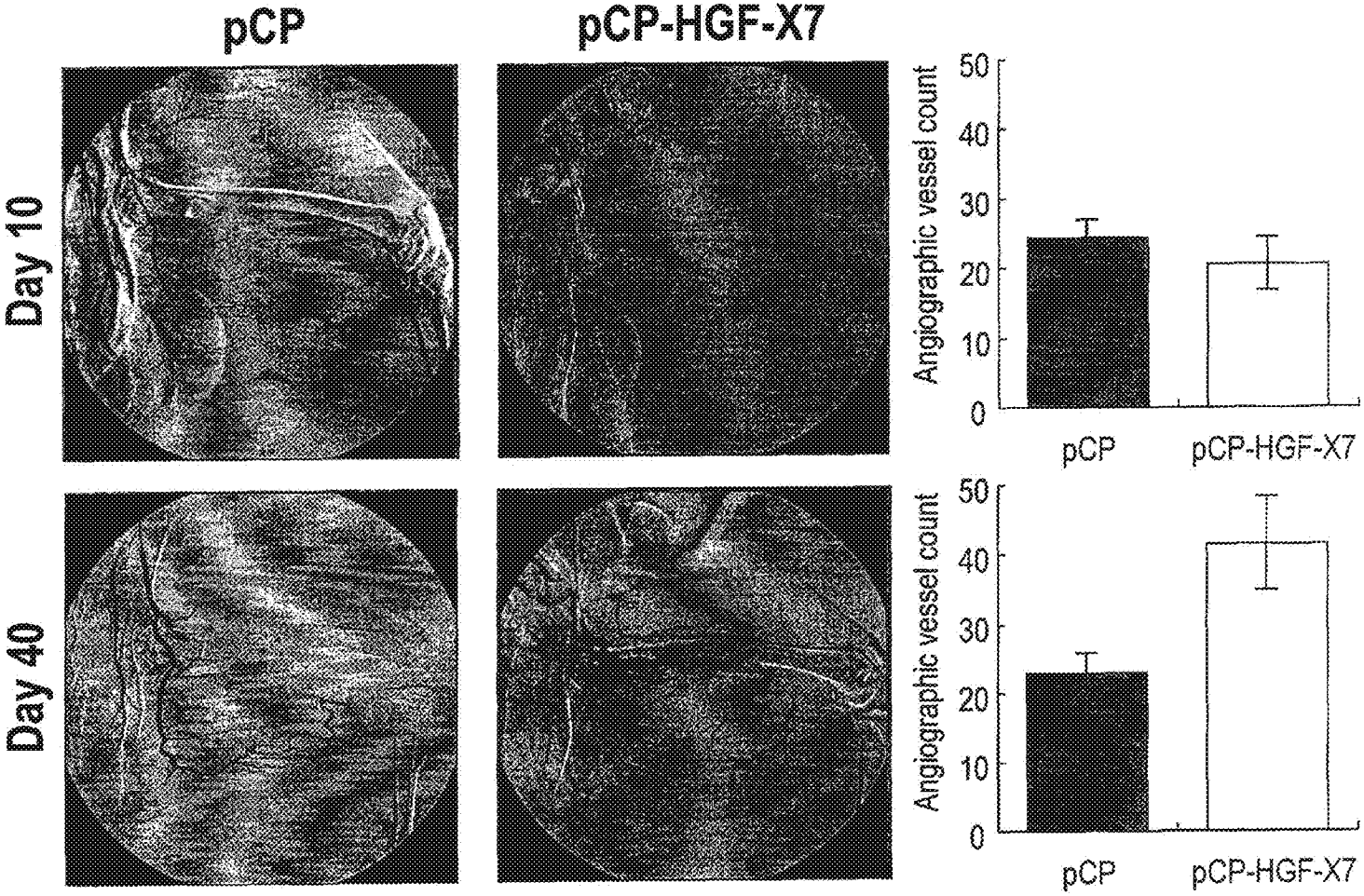
FIG. 11: cerebral angiogenesis of two groups of rabbits which were subject to administrating pCP and pCP-HGF-X7, respectively.

As can be seen from the result in FIG. 11, the degree of angiogenesis was significantly enhanced in the experimental group administered with pCP-HGF-X7 as compared with the pCP-administered control group.

This result demonstrates that HGF-X7 gene can be effectively used in the gene therapy of an ischemic disease.

While the invention has been described with respect to the above specific embodiments, it should be recognized that various modifications and changes may be made to the invention by those skilled in the art which also fall within the scope of the invention as defined by the appended claims.

---

SEQUENCE LISTING

```
<160> NUMBER OF SEQ ID NOS: 21

<210> SEQ ID NO 1
<211> LENGTH: 2187
<212> TYPE: DNA
<213> ORGANISM: Homo sapiens

<400> SEQUENCE: 1

atgtgggtga ccaaactcct gccagccctg ctgctgcagc atgtcctcct gcatctcctc      60

ctgctcccca tcgccatccc ctatgcagag ggacaaagga aaagaagaaa tacaattcat     120

gaattcaaaa aatcagcaaa gactacccta atcaaaatag atccagcact gaagataaaa     180

accaaaaaag tgaatactgc agaccaatgt gctaatagat gtactaggaa taaaggactt     240

ccattcactt gcaaggcttt tgtttttgat aaagcaagaa aacaatgcct ctggttcccc     300

ttcaatagca tgtcaagtgg agtgaaaaaa gaatttggcc atgaatttga cctctatgaa     360

aacaaagact acattagaaa ctgcatcatt ggtaaaggac gcagctacaa gggaacagta     420

tctatcacta agagtggcat caaatgtcag ccctggagtt ccatgatacc acacgaacac     480

agctttttgc cttcgagcta tcggggtaaa gacctacagg aaaactactg tcgaaatcct     540

cgaggggaag aagggggacc ctggtgtttc acaagcaatc cagaggtacg ctacgaagtc     600

tgtgacattc ctcagtgttc agaagttgaa tgcatgacct gcaatgggga gagttatcga     660

ggtctcatgg atcatacaga atcaggcaag atttgtcagc gctgggatca tcagacacca     720

caccggcaca aattcttgcc tgaaagatat cccgacaagg gctttgatga taattattgc     780

cgcaatcccg atggccagcc gaggccatgg tgctatactc ttgaccctca cacccgctgg     840

gagtactgtg caattaaaac atgcgctgac aatactatga atgacactga tgttcctttg     900

gaaacaactg aatgcatcca aggtcaagga gaaggctaca ggggcactgt caataccatt     960

tggaatggaa ttccatgtca gcgttgggat tctcagtatc ctcacgagca tgacatgact    1020
```

```
cctgaaaatt tcaagtgcaa ggacctacga gaaaattact gccgaaatcc agatgggtct   1080
gaatcaccct ggtgttttac cactgatcca aacatccgag ttggctactg ctcccaaatt   1140
ccaaactgtg atatgtcaca tggacaagat tgttatcgtg ggaatggcaa aaattatatg   1200
ggcaacttat cccaaacaag atctggacta acatgttcaa tgtgggacaa gaacatggaa   1260
gacttacatc gtcatatctt ctgggaacca gatgcaagta agctgaatga gaattactgc   1320
cgaaatccag atgatgatgc tcatggaccc tggtgctaca cgggaaatcc actcattcct   1380
tgggattatt gccctatttc tcgttgtgaa ggtgatacca cacctacaat agtcaattta   1440
gaccatcccg taatatcttg tgccaaaacg aaacaattgc gagttgtaaa tgggattcca   1500
acacgaacaa acataggatg gatggttagt ttgagataca gaaataaaca tatctgcgga   1560
ggatcattga taaaggagag ttgggttctt actgcacgac agtgtttccc ttctcgagac   1620
ttgaaagatt atgaagcttg gcttggaatt catgatgtcc acggaagagg agatgagaaa   1680
tgcaaacagg ttctcaatgt ttcccagctg gtatatggcc ctgaaggatc agatctggtt   1740
ttaatgaagc ttgccaggcc tgctgtcctg gatgattttg ttagtacgat tgatttacct   1800
aattatggat gcacaattcc tgaaaagacc agttgcagtg tttatggctg gggctacact   1860
ggattgatca actatgatgg cctattacga gtggcacatc tctatataat gggaaatgag   1920
aaatgcagcc agcatcatcg agggaaggtg actctgaatg agtctgaaat atgtgctggg   1980
gctgaaaaga ttggatcagg accatgtgag ggggattatg gtggcccact tgtttgtgag   2040
caacataaaa tgagaatggt tcttggtgtc attgttcctg gtcgtggatg tgccattcca   2100
aatcgtcctg gtatttttgt ccgagtagca tattatgcaa aatggataca caaaattatt   2160
ttaacatata aggtaccaca gtcatag                                       2187
```

<210> SEQ ID NO 2
<211> LENGTH: 7113
<212> TYPE: DNA
<213> ORGANISM: Homo sapiens

<400> SEQUENCE: 2

```
atgtgggtga ccaaactcct gccagccctg ctgctgcagc atgtcctcct gcatctcctc     60
ctgctcccca tcgccatccc ctatgcagag ggacaaagga aaagaagaaa tacaattcat    120
gaattcaaaa aatcagcaaa gactacccta atcaaaatag atccagcact gaagataaaa    180
accaaaaaag tgaatactgc agaccaatgt gctaatagat gtactaggaa taaaggactt    240
ccattcactt gcaaggcttt tgtttttgat aaagcaagaa aacaatgcct ctggttcccc    300
ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
tctatcacta agagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa aacaatatct taccttaatg cctcaatttg tagatctcgg    720
tatttgtgaa ataataacgt aaacttcgtt taaaaggatt cttcttcctg tctttgagaa    780
agtacggcac tgtgcagggg gagaggttga ttgtgaaaaa tcagaggtag atgagaatct    840
tactgagggc tgagggttct ttaaccttgg tggatctcaa cattggttgc acattaaaat    900
```

-continued

```
cacctgctgc aagcccttga cgaatcttac ttagaagatg acaacacaga acaattaaat    960
cagaatctct ggggagaata gggcaccagt atttttgag ctcccaccat gattccaaag   1020
tgcagccaaa tttgagaacc actgctaaaa gctcaagctt cagattgacc agcttttcca   1080
tctcacctat cgcctaaaga ccaaattgga taaatgtgtt cattacgaca gatgggtact   1140
atttaaagat gagtaaacac aatatactta ggctcgtcag actgagagtt ttaatcatca   1200
ctgaggaaaa acatagatat ctaatactga ctggagtatt agtcaaggct tatttcacac   1260
acaattttat cagaaaccaa agtagtttaa aacagctctc cccttattag taatgcattg   1320
gagggtttac tttaccatgt accttgctga gcactgtacc ttgttaatct catttacttg   1380
taatgagaac cacacagcgg gtagttttat tggttctatt ttacctacat gacaaaactg   1440
aagcataaaa acacttagta agttttcagt gtcatgcaca actaggaagt gacatggcca   1500
gaatataagc ccagtcacca tcactctata acctgcgctt ttaacaactt cagggcatga   1560
cacatttggc cggtcagtag aacccatgct gtgatttgtt tttgcagtgg tggtgatgac   1620
tgccttgttg aatccacttt ttattctatt ccattttggg gacacaattc tgcaagatga   1680
ttcttcatta ggaaacagag atgagttatt gaccaacaca gaaagaaaaa gagtttgttg   1740
ctccacactg ggattaaacc tatgatcttg gcctaattaa cactagctag taagtgtcca   1800
agctgatcat ctctacaaca tttcaataac agaaaacaac aattttcaaa attagttact   1860
tacaattatg tagaaatgcc tctaaaacac agtattttcc ttatattaca aaaacaaaaa   1920
ttataattgg ttttgtcctc ttttgagagt ttgcatggtg ttactccctg catagtgaag   1980
aaaacatttt atttaagtag atggatctaa gtttttcatg aacaaaggaa tgacatttga   2040
aatcaatcct accctagtcc aggagaatgc attagattaa cctagtagag gtcttatttc   2100
accctgagtt ttctatgatc gtgattctct gctggaggag taattgtgaa atagatctct   2160
ctgggaactg gcttcctagt ccaatcagct cttttaccaa tgaacacttc cttgtgatat   2220
agatgtttat ggccgagagg atccagtata ttaataaaat cccttttgt attcaatgag   2280
ggaaacacat aattttcatc aattagcagc ttattggaat atctgcatga tggtttaaca   2340
cttttaagtg ttgactaaag attaatttta cagaaaatag aaaaagaaat atgtttctgt   2400
ctggaggaat gatttattgt tgacccctaa attgaaatat tttactagtg gcttaatgga   2460
aagatgatga aagatgatga aattaatgta gaagcttaac tagaaaatca ggtgacctga   2520
tatctacatc tgtatccttc attggccacc cagcattcat taatgaatca gatgatggaa   2580
tagatcaagt ttcctaggaa cacagtgaat attaaaagaa aacaaaggga gcctagcacc   2640
tagaagacct agtttatatt tcaaagtata tttggatgta acccaatttt aaacatttcc   2700
tcacttgtct ctcttaaagc cttgccaaca gcaaggacag agaaccaaaa atagtgtata   2760
tatgaataaa tgcttattac agaatctgct gactggcaca tgctttgtgt gtaatgggtt   2820
ctcataaaca cttgttgaat gaacacacat aagtgaaaga gcatggctag gcttcatccc   2880
ttggtcaaat atggggtgct aaagaaaagc aggggaaata cattgggaca ctaacaaaaa   2940
aaaacagtta atttaggtaa aagataaaat acaccacaga atgaagaaaa gagatgaccc   3000
agactgctct ttaaccttca tgtcctagag aggtttttga tatgaattgc attcagaatt   3060
gtggaaagga gcccatcttt tctcttcatt ttgattttat taactccaat gggggaattt   3120
tattcgtgtt ttggccatat ctacttttga tttctacatt attctctctt cctttctacc   3180
tgtatttgtc ctaataaatt gttgacttat taattcacta cttcctcaca gctttttttt   3240
ggctttacaa atccactgga aaggtatatg ggtgtatcac tttgtgtatt tcggtgtgca   3300
```

```
tgtgtagagg ggacaaaaat cctctctcaa actataaata ttgagtattt gtgtattgaa   3360
catttgctat aactactagg tttcttaaat aatcttaata tataaaatga tatagaaaaa   3420
gggaaattat agttcgtatt attcatctaa gtgaagagat taaaacccag ggagtaaata   3480
aattgtctaa ggactaaggt tgtatactat ttaggtgata gatatggggc aaccgtatgg   3540
gttttatgat taacaaataa acttctcacc actctaccat atcaactttt ccataaaaga   3600
gagctatagt attctttgct taaataaatt tgattagtgc atgacttctt gaaaacatat   3660
aaagcaaaag tcacatttga ttctatcaga aaagtgagta agccatggcc caaacaaaag   3720
atgcattaaa atattctgga atgatggagc taaaagtaag aaaaatgact ttttaaaaaa   3780
gtttactgtt aggaattgtg aaattatgct gaattttagt tgcattataa tttttgtcag   3840
tcatacggtc tgacaacctg tcttatttct atttccccat atgaggaatg ctagttaagt   3900
atggatatta actattacta cttagatgca ttgaagttgc ataatatgga taatacttca   3960
ctggttccct gaaaatgttt agttagtaat aagtctctta cactatttgt tttgtccaat   4020
aatttatatt ttctgaagac ttaactctag aatacactca tgtcaaaatg aaagaatttc   4080
attgcaaaat attgcttggt acatgacgca tacctgtatt tgttttgtgt cacaacatga   4140
aaaatgatgg tttattagaa gtttcattgg gtaggaaaca catttgaatg gtatttacta   4200
agatactaaa atccttggac ttcactctaa ttttagtgcc atttagaact caaggtctca   4260
gtaaaagtag aaataaagcc tgttaacaaa acacaagctg aatattaaaa atgtaactgg   4320
attttcaaag aaatgtttac tggtattacc tgtagatgta tattctttat tatgatcttt   4380
tgtgtaaagt ctggcagaca aatgcaatat ctaattgttg agtccaatat cacaagcagt   4440
acaaaagtat aaaaaagact tggccttttc taatgtgtta aaatacttta tgctggtaat   4500
aacactaaga gtagggcact agaaatttta agtgaagata atgtgttgca gttactgcac   4560
tcaatggctt actattataa accaaaactg ggatcactaa gctccagtca gtcaaaatga   4620
tcaaaattat tgaagagaat aagcaattct gttctttatt aggacacagt agatacagac   4680
tacaaagtgg agtgtgctta ataagaggta gcatttgtta agtgtcaatt actctattat   4740
cccttggagc ttctcaaaat aaccatataa ggtgtaagat gttaaaggtt atggttacac   4800
tcagtgcaca ggtaagctaa taggctgaga gaagctaaat tacttactgg ggtctcacag   4860
taagaaagtg agctgaagtt tcagcccaga tttaactgga ttctgggctc tttattcatg   4920
ttacttcatg aatctgtttc tcaattgtgc agaaaaaagg gggctattta taagaaaagc   4980
aataaacaaa caagtaatga tctcaaataa gtaatgcaag aaatagtgag atttcaaaat   5040
cagtggcagc gatttctcag ttctgtccta agtggccttg ctcaatcacc tgctatcttt   5100
tagtggagct ttgaaattat gtttcagaca acttcgattc agttctagaa tgtttgactc   5160
agcaaattca caggctcatc tttctaactt gatggtgaat atggaaattc agctaaatgg   5220
atgttaataa aattcaaacg ttttaaggac agatgaaaat gacagaattt taaggtaaaa   5280
tatatgaagg aatataagat aaaggatttt tctaccttca gcaaaaacat acccactaat   5340
tagtaaaatt aataggcaaa aaaaagttgc atgctcttat actgtaatga ttatcatttt   5400
aaaactagct ttttgccttc gagctatcgg ggtaaagacc tacaggaaaa ctactgtcga   5460
aatcctcgag gggaagaagg gggaccctgg tgtttcacaa gcaatccaga ggtacgctac   5520
gaagtctgtg acattcctca gtgttcagaa gttgaatgca tgacctgcaa tggggagagt   5580
tatcgaggtc tcatggatca tacagaatca ggcaagattt gtcagcgctg ggatcatcag   5640
```

```
acaccacacc ggcacaaatt cttgcctgaa agatatcccg acaagggctt tgatgataat   5700

tattgccgca atcccgatgg ccagccgagg ccatggtgct atactcttga ccctcacacc   5760

cgctgggagt actgtgcaat taaaacatgc gctgacaata ctatgaatga cactgatgtt   5820

cctttggaaa caactgaatg catccaaggt caaggagaag gctacagggg cactgtcaat   5880

accatttgga atggaattcc atgtcagcgt tgggattctc agtatcctca cgagcatgac   5940

atgactcctg aaaatttcaa gtgcaaggac ctacgagaaa attactgccg aaatccagat   6000

gggtctgaat caccctggtg ttttaccact gatccaaaca tccgagttgg ctactgctcc   6060

caaattccaa actgtgatat gtcacatgga caagattgtt atcgtgggaa tggcaaaaat   6120

tatatgggca acttatccca aacaagatct ggactaacat gttcaatgtg ggacaagaac   6180

atggaagact tacatcgtca tatcttctgg gaaccagatg caagtaagct gaatgagaat   6240

tactgccgaa atccagatga tgatgctcat ggaccctggt gctacacggg aaatccactc   6300

attccttggg attattgccc tatttctcgt tgtgaaggtg ataccacacc tacaatagtc   6360

aatttagacc atcccgtaat atcttgtgcc aaaacgaaac aattgcgagt tgtaaatggg   6420

attccaacac gaacaaacat aggatggatg gttagtttga gatacagaaa taaacatatc   6480

tgcggaggat cattgataaa ggagagttgg gttcttactg cacgacagtg tttcccttct   6540

cgagacttga aagattatga agcttggctt ggaattcatg atgtccacgg aagaggagat   6600

gagaaatgca aacaggttct caatgtttcc cagctggtat atggccctga aggatcagat   6660

ctggttttaa tgaagcttgc caggcctgct gtcctggatg attttgttag tacgattgat   6720

ttacctaatt atggatgcac aattcctgaa aagaccagtt gcagtgttta tggctggggc   6780

tacactggat tgatcaacta tgatggccta ttacgagtgg cacatctcta tataatggga   6840

aatgagaaat gcagccagca tcatcgaggg aaggtgactc tgaatgagtc tgaaatatgt   6900

gctggggctg aaaagattgg atcaggacca tgtgaggggg attatggtgg cccacttgtt   6960

tgtgagcaac ataaaatgag aatggttctt ggtgtcattg ttcctggtcg tggatgtgcc   7020

attccaaatc gtcctggtat ttttgtccga gtagcatatt atgcaaaatg gatacacaaa   7080

attattttaa catataaggt accacagtca tag                                7113
```

<210> SEQ ID NO 3
<211> LENGTH: 34
<212> TYPE: DNA
<213> ORGANISM: Artificial Sequence
<220> FEATURE:
<223> OTHER INFORMATION: gHGF3 primer

<400> SEQUENCE: 3

```
gtaaaggacg cgtctacaag ggaacagtat ctat                                 34
```

<210> SEQ ID NO 4
<211> LENGTH: 27
<212> TYPE: DNA
<213> ORGANISM: Artificial Sequence
<220> FEATURE:
<223> OTHER INFORMATION: gHGF4 primer

<400> SEQUENCE: 4

```
actggatcct ctcggccata aacatct                                         27
```

<210> SEQ ID NO 5
<211> LENGTH: 34
<212> TYPE: DNA
<213> ORGANISM: Artificial Sequence <220> FEATURE:
<223> OTHER INFORMATION: gHGF10 primer

<400> SEQUENCE: 5 gaagcttagc accatgtggg tgaccaaact cctg 34

<210> SEQ ID NO 6
<211> LENGTH: 27
<212> TYPE: DNA
<213> ORGANISM: Artificial Sequence
<220> FEATURE:
<223> OTHER INFORMATION: gHGF5 primer

<400> SEQUENCE: 6 tggccgagag gatccagtat attaata 27

<210> SEQ ID NO 7
<211> LENGTH: 27
<212> TYPE: DNA
<213> ORGANISM: Artificial Sequence
<220> FEATURE:
<223> OTHER INFORMATION: gHGF7 primer

<400> SEQUENCE: 7 cccctcgagg atttcgacag tagtttt 27

<210> SEQ ID NO 8
<211> LENGTH: 28
<212> TYPE: DNA
<213> ORGANISM: Artificial Sequence
<220> FEATURE:
<223> OTHER INFORMATION: gHGF12 primer

<400> SEQUENCE: 8 gggatccctt cctttctacc tgtatttg 28

<210> SEQ ID NO 9
<211> LENGTH: 25
<212> TYPE: DNA
<213> ORGANISM: Artificial Sequence
<220> FEATURE:
<223> OTHER INFORMATION: gHGF13 primer

<400> SEQUENCE: 9 gggatcctgg gtaaacacat ttgaa 25

<210> SEQ ID NO 10
<211> LENGTH: 28
<212> TYPE: DNA
<213> ORGANISM: Artificial Sequence
<220> FEATURE:
<223> OTHER INFORMATION: gHGF6 primer

<400> SEQUENCE: 10 gggatcctta tgtttcagac aacttcga 28

<210> SEQ ID NO 11
<211> LENGTH: 34
<212> TYPE: DNA
<213> ORGANISM: Artificial Sequence
<220> FEATURE:
<223> OTHER INFORMATION: gHGF1 primer

<400> SEQUENCE: 11 gaagcttgcc accatgtggg tgaccaaact cctg 34

<210> SEQ ID NO 12
<211> LENGTH: 34
<212> TYPE: DNA
<213> ORGANISM: Artificial Sequence
<220> FEATURE:
<223> OTHER INFORMATION: gHGF2 primer

<400> SEQUENCE: 12 gggatccaga acgcgtcctt taccgatgat gcag 34

<210> SEQ ID NO 13
<211> LENGTH: 35
<212> TYPE: DNA
<213> ORGANISM: Artificial Sequence
<220> FEATURE:
<223> OTHER INFORMATION: gHGF8 primer

<400> SEQUENCE: 13 gggatccctt ctcgagactt gaaagattat gaagc 35

<210> SEQ ID NO 14
<211> LENGTH: 32
<212> TYPE: DNA
<213> ORGANISM: Artificial Sequence
<220> FEATURE:
<223> OTHER INFORMATION: gHGF9 primer

<400> SEQUENCE: 14 gtctagagcg gccgctatga ctgtggtacc tt 32

<210> SEQ ID NO 15
<211> LENGTH: 36
<212> TYPE: DNA
<213> ORGANISM: Artificial Sequence
<220> FEATURE:
<223> OTHER INFORMATION: cHGF5 primer

<400> SEQUENCE: 15 ggatccacgc gtagcagcac catgtgggtg accaaa 36

<210> SEQ ID NO 16
<211> LENGTH: 36
<212> TYPE: DNA
<213> ORGANISM: Artificial Sequence
<220> FEATURE:
<223> OTHER INFORMATION: cHGF3 primer

<400> SEQUENCE: 16 ggatcctcta gattacttca gctatgactg tggtac 36

<210> SEQ ID NO 17
<211> LENGTH: 26
<212> TYPE: DNA
<213> ORGANISM: Artificial Sequence
<220> FEATURE:
<223> OTHER INFORMATION: GHGF5' primer

<400> SEQUENCE: 17 caaatgtcag ccctggagtt ccatga 26

<210> SEQ ID NO 18
<211> LENGTH: 23
<212> TYPE: DNA
<213> ORGANISM: Artificial Sequence
<220> FEATURE:
<223> OTHER INFORMATION: GHGF3' primer

<400> SEQUENCE: 18 ctggattgct tgtgaaacag ggt 23

<210> SEQ ID NO 19
<211> LENGTH: 4679
<212> TYPE: DNA
<213> ORGANISM: Artificial Sequence
<220> FEATURE:
<223> OTHER INFORMATION: HGF-X6 gene

<400> SEQUENCE: 19 atgtgggtga ccaaactcct gccagccctg ctgctgcagc atgtcctcct gcatctcctc 60 ctgctcccca tcgccatccc ctatgcagag ggacaaagga aaagaagaaa tacaattcat 120 gaattcaaaa aatcagcaaa gactacccta atcaaaatag atccagcact gaagataaaa 180 accaaaaaag tgaatactgc agaccaatgt gctaatagat gtactaggaa taaaggactt 240 ccattcactt gcaaggcttt tgtttttgat aaagcaagaa aacaatgcct ctggttcccc 300 ttcaatagca tgtcaagtgg agtgaaaaaa gaatttggcc atgaatttga cctctatgaa 360 aacaaagact acattagaaa ctgcatcatc ggtaaaggac gcagctacaa gggaacagta 420 tctatcacta agagtggcat caaatgtcag ccctggagtt ccatgatacc acacgaacac 480 aggtaagaac agtatgaaga aaagagatga agcctctgtc ttttttacat gttaacagtc 540 tcatattagt ccttcagaat aattctacaa tcctaaaata acttagccaa cttgctgaat 600 tgtattacgg caaggtttat atgaattcat gactgatatt tagcaaatga ttaattaata 660 tgttaataaa atgtagccaa aacaatatct taccttaatg cctcaatttg tagatctcgg 720 tatttgtgga tcccttcctt tctacctgta tttgtcctaa taaattgttg acttattaat 780 tcactacttc ctcacagctt ttttttggct ttacaaatcc actggaaagg tatatgggtg 840 tatcactttg tgtatttcgg tgtgcatgtg tagaggggac aaaaatcctc tctcaaacta 900 taaatattga gtatttgtgt attgaacatt tgctataact actaggtttc ttaaataatc 960 ttaatatata aaatgatata gaaaaaggga aattatagtt cgtattattc atctaagtga 1020 agagattaaa acccagggag taaataaatt gtctaaggac taaggttgta tactatttag 1080 gtgatagata tggggcaacc gtatgggttt tatgattaac aaataaactt ctcaccactc 1140 taccatatca acttttccat aaaagagagc tatagtattc tttgcttaaa taaatttgat 1200 tagtgcatga cttcttgaaa acatataaag caaaagtcac atttgattct atcagaaaag 1260 tgagtaagcc atggcccaaa caaaagatgc attaaaatat tctggaatga tggagctaaa 1320 agtaagaaaa atgacttttt aaaaaagttt actgttagga attgtgaaat tatgctgaat 1380 tttagttgca ttataatttt tgtcagtcat acggtctgac aacctgtctt atttctattt 1440 ccccatatga ggaatgctag ttaagtatgg atattaacta ttactactta gatgcattga 1500 agttgcataa tatggataat acttcactgg ttccctgaaa atgtttagtt agtaataagt 1560 ctcttacact atttgttttg tccaataatt tatattttct gaagacttaa ctctagaata 1620 cactcatgtc aaaatgaaag aatttcattg caaaatattg cttggtacat gacgcatacc 1680 tgtatttgtt ttgtgtcaca acatgaaaaa tgatggttta ttagaagttt cattgggtag 1740 gaaacacatt tgaatggtat ttactaagat actaaaatcc ttggacttca ctctaatttt 1800 agtgccattt agaactcaag gtctcagtaa aagtagaaat aaagcctgtt aacaaaacac 1860 aagctgaata ttaaaaatgt aactggattt tcaaagaaat gtttactggt attacctgta 1920

```
gatgtatatt ctttattatg atcttttgtg taaagtctgg cagacaaatg caatatctaa   1980
ttgttgagtc caatatcaca agcagtacaa aagtataaaa aagacttggc cttttctaat   2040
gtgttaaaat actttatgct ggtaataaca ctaagagtag ggcactagaa attttaagtg   2100
aagataatgt gttgcagtta ctgcactcaa tggcttacta ttataaacca aaactgggat   2160
cactaagctc cagtcagtca aaatgatcaa aattattgaa gagaataagc aattctgttc   2220
tttattagga cacagtagat acagactaca aagtggagtg tgcttaataa gaggtagcat   2280
ttgttaagtg tcaattactc tattatccct tggagcttct caaaataacc atataaggtg   2340
taagatgtta aaggttatgg ttacactcag tgcacaggta agctaatagg ctgagagaag   2400
ctaaattact tactggggtc tcacagtaag aaagtgagct gaagtttcag cccagattta   2460
actggattct gggctcttta ttcatgttac ttcatgaatc tgtttctcaa ttgtgcagaa   2520
aaaagggggc tatttataag aaaagcaata aacaaacaag taatgatctc aaataagtaa   2580
tgcaagaaat agtgagattt caaaatcagt ggcagcgatt tctcagttct gtcctaagtg   2640
gccttgctca atcacctgct atcttttagt ggagctttga aattatgttt cagacaactt   2700
cgattcagtt ctagaatgtt tgactcagca aattcacagg ctcatctttc taacttgatg   2760
gtgaatatgg aaattcagct aaatggatgt taataaaatt caaacgtttt aaggacagat   2820
gaaaatgaca gaattttaag gtaaaatata tgaaggaata taagataaag gatttttcta   2880
ccttcagcaa aaacataccc actaattagt aaaattaata ggcaaaaaaa agttgcatgc   2940
tcttatactg taatgattat cattttaaaa ctagcttttt gccttcgagc tatcggggta   3000
aagacctaca ggaaaactac tgtcgaaatc ctcgagggga agaaggggga ccctggtgtt   3060
tcacaagcaa tccagaggta cgctacgaag tctgtgacat tcctcagtgt tcagaagttg   3120
aatgcatgac ctgcaatggg gagagttatc gaggtctcat ggatcataca gaatcaggca   3180
agatttgtca gcgctgggat catcagacac cacaccggca caaattcttg cctgaaagat   3240
atcccgacaa gggctttgat gataattatt gccgcaatcc cgatggccag ccgaggccat   3300
ggtgctatac tcttgaccct cacacccgct gggagtactg tgcaattaaa acatgcgctg   3360
acaatactat gaatgacact gatgttcctt tggaaacaac tgaatgcatc caaggtcaag   3420
gagaaggcta caggggcact gtcaatacca tttggaatgg aattccatgt cagcgttggg   3480
attctcagta tcctcacgag catgacatga ctcctgaaaa tttcaagtgc aaggacctac   3540
gagaaaatta ctgccgaaat ccagatgggt ctgaatcacc ctggtgtttt accactgatc   3600
caaacatccg agttggctac tgctcccaaa ttccaaactg tgatatgtca catggacaag   3660
attgttatcg tgggaatggc aaaaattata tgggcaactt atcccaaaca agatctggac   3720
taacatgttc aatgtgggac aagaacatgg aagacttaca tcgtcatatc ttctgggaac   3780
cagatgcaag taagctgaat gagaattact gccgaaatcc agatgatgat gctcatggac   3840
cctggtgcta cacgggaaat ccactcattc cttgggatta ttgccctatt tctcgttgtg   3900
aaggtgatac cacacctaca atagtcaatt tagaccatcc cgtaatatct tgtgccaaaa   3960
cgaaacaatt gcgagttgta aatgggattc caacacgaac aaacatagga tggatggtta   4020
gtttgagata cagaaataaa catatctgcg gaggatcatt gataaaggag agttgggttc   4080
ttactgcacg acagtgtttc ccttctcgag acttgaaaga ttatgaagct tggcttggaa   4140
ttcatgatgt ccacggaaga ggagatgaga aatgcaaaca ggttctcaat gtttcccagc   4200
tggtatatgg ccctgaagga tcagatctgg ttttaatgaa gcttgccagg cctgctgtcc   4260
tggatgattt tgttagtacg attgatttac ctaattatgg atgcacaatt cctgaaaaga   4320
```

```
ccagttgcag tgtttatggc tggggctaca ctggattgat caactatgat ggcctattac   4380

gagtggcaca tctctatata atgggaaatg agaaatgcag ccagcatcat cgagggaagg   4440

tgactctgaa tgagtctgaa atatgtgctg gggctgaaaa gattggatca ggaccatgtg   4500

agggggatta tggtggccca cttgtttgtg agcaacataa aatgagaatg gttcttggtg   4560

tcattgttcc tggtcgtgga tgtgccattc caaatcgtcc tggtattttt gtccgagtag   4620

catattatgc aaaatggata cacaaaatta ttttaacata taaggtacca cagtcatag    4679
```

<210> SEQ ID NO 20
<211> LENGTH: 3679
<212> TYPE: DNA
<213> ORGANISM: Artificial Sequence
<220> FEATURE:
<223> OTHER INFORMATION: HGF-X7 gene

<400> SEQUENCE: 20

```
atgtgggtga ccaaactcct gccagccctg ctgctgcagc atgtcctcct gcatctcctc     60

ctgctcccca tcgccatccc ctatgcagag ggacaaagga aaagaagaaa tacaattcat    120

gaattcaaaa aatcagcaaa gactacccta atcaaaatag atccagcact gaagataaaa    180

accaaaaaag tgaatactgc agaccaatgt gctaatagat gtactaggaa taaaggactt    240

ccattcactt gcaaggcttt tgtttttgat aaagcaagaa aacaatgcct ctggttcccc    300

ttcaatagca tgtcaagtgg agtgaaaaaa gaatttggcc atgaatttga cctctatgaa    360

aacaaagact acattagaaa ctgcatcatc ggtaaaggac gcagctacaa gggaacagta    420

tctatcacta agagtggcat caaatgtcag ccctggagtt ccatgatacc acacgaacac    480

aggtaagaac agtatgaaga aaagagatga agcctctgtc ttttttacat gttaacagtc    540

tcatattagt ccttcagaat aattctacaa tcctaaaata acttagccaa cttgctgaat    600

tgtattacgg caaggtttat atgaattcat gactgatatt tagcaaatga ttaattaata    660

tgttaataaa atgtagccaa aacaatatct taccttaatg cctcaatttg tagatctcgg    720

tatttgtgga tcctgggtag gaaacacatt tgaatggtat ttactaagat actaaaatcc    780

ttggacttca ctctaatttt agtgccattt agaactcaag gtctcagtaa aagtagaaat    840

aaagcctgtt aacaaaacac aagctgaata ttaaaaatgt aactggattt tcaaagaaat    900

gtttactggt attacctgta gatgtatatt ctttattatg atcttttgtg taaagtctgg    960

cagacaaatg caatatctaa ttgttgagtc caatatcaca agcagtacaa aagtataaaa   1020

aagacttggc cttttctaat gtgttaaaat actttatgct ggtaataaca ctaagagtag   1080

ggcactagaa attttaagtg aagataatgt gttgcagtta ctgcactcaa tggcttacta   1140

ttataaacca aaactgggat cactaagctc cagtcagtca aaatgatcaa aattattgaa   1200

gagaataagc aattctgttc tttattagga cacagtagat acagactaca aagtggagtg   1260

tgcttaataa gaggtagcat ttgttaagtg tcaattactc tattatccct tggagcttct   1320

caaaataacc atataaggtg taagatgtta aaggttatgg ttacactcag tgcacaggta   1380

agctaatagg ctgagagaag ctaaattact tactggggtc tcacagtaag aaagtgagct   1440

gaagtttcag cccagattta actggattct gggctcttta ttcatgttac ttcatgaatc   1500

tgtttctcaa ttgtgcagaa aaaagggggc tatttataag aaaagcaata aacaaacaag   1560

taatgatctc aaataagtaa tgcaagaaat agtgagattt caaaatcagt ggcagcgatt   1620

tctcagttct gtcctaagtg gccttgctca atcacctgct atcttttagt ggagctttga   1680
```

```
aattatgttt cagacaactt cgattcagtt ctagaatgtt tgactcagca aattcacagg   1740
ctcatctttc taacttgatg gtgaatatgg aaattcagct aaatggatgt taataaaatt   1800
caaacgtttt aaggacagat gaaaatgaca gaattttaag gtaaaatata tgaaggaata   1860
taagataaag gatttttcta ccttcagcaa aaacataccc actaattagt aaaattaata   1920
ggcaaaaaaa agttgcatgc tcttatactg taatgattat cattttaaaa ctagcttttt   1980
gccttcgagc tatcggggta aagacctaca ggaaaactac tgtcgaaatc ctcgagggga   2040
agaaggggga ccctggtgtt tcacaagcaa tccagaggta cgctacgaag tctgtgacat   2100
tcctcagtgt tcagaagttg aatgcatgac ctgcaatggg gagagttatc gaggtctcat   2160
ggatcataca gaatcaggca agatttgtca gcgctgggat catcagacac cacaccggca   2220
caaattcttg cctgaaagat atcccgacaa gggctttgat gataattatt gccgcaatcc   2280
cgatggccag ccgaggccat ggtgctatac tcttgaccct cacacccgct gggagtactg   2340
tgcaattaaa acatgcgctg acaatactat gaatgacact gatgttcctt tggaaacaac   2400
tgaatgcatc caaggtcaag gagaaggcta caggggcact gtcaatacca tttggaatgg   2460
aattccatgt cagcgttggg attctcagta tcctcacgag catgacatga ctcctgaaaa   2520
tttcaagtgc aaggacctac gagaaaatta ctgccgaaat ccagatgggt ctgaatcacc   2580
ctggtgtttt accactgatc caaacatccg agttggctac tgctcccaaa ttccaaactg   2640
tgatatgtca catggacaag attgttatcg tgggaatggc aaaaattata tgggcaactt   2700
atcccaaaca agatctggac taacatgttc aatgtgggac aagaacatgg aagacttaca   2760
tcgtcatatc ttctgggaac cagatgcaag taagctgaat gagaattact gccgaaatcc   2820
agatgatgat gctcatggac cctggtgcta cacgggaaat ccactcattc cttgggatta   2880
ttgccctatt tctcgttgtg aaggtgatac cacacctaca atagtcaatt tagaccatcc   2940
cgtaatatct tgtgccaaaa cgaaacaatt gcgagttgta aatgggattc caacacgaac   3000
aaacatagga tggatggtta gtttgagata cagaaataaa catatctgcg gaggatcatt   3060
gataaaggag agttgggttc ttactgcacg acagtgtttc ccttctcgag acttgaaaga   3120
ttatgaagct tggcttggaa ttcatgatgt ccacggaaga ggagatgaga aatgcaaaca   3180
ggttctcaat gtttcccagc tggtatatgg ccctgaagga tcagatctgg ttttaatgaa   3240
gcttgccagg cctgctgtcc tggatgattt tgttagtacg attgatttac ctaattatgg   3300
atgcacaatt cctgaaaaga ccagttgcag tgtttatggc tggggctaca ctggattgat   3360
caactatgat ggcctattac gagtggcaca tctctatata atgggaaatg agaaatgcag   3420
ccagcatcat cgagggaagg tgactctgaa tgagtctgaa atatgtgctg gggctgaaaa   3480
gattggatca ggaccatgtg agggggatta tggtggccca cttgtttgtg agcaacataa   3540
aatgagaatg gttcttggtg tcattgttcc tggtcgtgga tgtgccattc caaatcgtcc   3600
tggtattttt gtccgagtag catattatgc aaaatggata cacaaaatta ttttaacata   3660
taaggtacca cagtcatag                                                3679
```

<210> SEQ ID NO 21
<211> LENGTH: 2729
<212> TYPE: DNA
<213> ORGANISM: Artificial Sequence
<220> FEATURE:
<223> OTHER INFORMATION: HGF-X8 gene

<400> SEQUENCE: 21

```
atgtgggtga ccaaactcct gccagccctg ctgctgcagc atgtcctcct gcatctcctc     60
```

```
ctgctcccca tcgccatccc ctatgcagag ggacaaagga aaagaagaaa tacaattcat    120
gaattcaaaa aatcagcaaa gactacccta atcaaaatag atccagcact gaagataaaa    180
accaaaaaag tgaatactgc agaccaatgt gctaatagat gtactaggaa taaaggactt    240
ccattcactt gcaaggcttt tgtttttgat aaagcaagaa aacaatgcct ctggttcccc    300
ttcaatagca tgtcaagtgg agtgaaaaaa gaatttggcc atgaatttga cctctatgaa    360
aacaaagact acattagaaa ctgcatcatc ggtaaaggac gcagctacaa gggaacagta    420
tctatcacta agagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa aacaatatct taccttaatg cctcaatttg tagatctcgg    720
tatttgtgga tccttatgtt tcagacaact tcgattcagt tctagaatgt ttgactcagc    780
aaattcacag gctcatcttt ctaacttgat ggtgaatatg gaaattcagc taaatggatg    840
ttaataaaat tcaaacgttt taaggacaga tgaaaatgac agaattttaa ggtaaaatat    900
atgaaggaat ataagataaa ggatttttct accttcagca aaaacatacc cactaattag    960
taaaattaat aggcaaaaaa aagttgcatg ctcttatact gtaatgatta tcattttaaa   1020
actagctttt tgccttcgag ctatcggggt aaagacctac aggaaaacta ctgtcgaaat   1080
cctcgagggg aagaaggggg accctggtgt ttcacaagca atccagaggt acgctacgaa   1140
gtctgtgaca ttcctcagtg ttcagaagtt gaatgcatga cctgcaatgg ggagagttat   1200
cgaggtctca tggatcatac agaatcaggc aagatttgtc agcgctggga tcatcagaca   1260
ccacaccggc acaaattctt gcctgaaaga tatcccgaca agggctttga tgataattat   1320
tgccgcaatc ccgatggcca gccgaggcca tggtgctata ctcttgaccc tcacacccgc   1380
tgggagtact gtgcaattaa aacatgcgct gacaatacta tgaatgacac tgatgttcct   1440
ttggaaacaa ctgaatgcat ccaaggtcaa ggagaaggct acaggggcac tgtcaatacc   1500
atttggaatg gaattccatg tcagcgttgg gattctcagt atcctcacga gcatgacatg   1560
actcctgaaa atttcaagtg caaggaccta cgagaaaatt actgccgaaa tccagatggt   1620
ctgaatcacc ctggtgtttt accactgatc caaacatccg agttggctac tgctcccaaa   1680
ttccaaactg tgatatgtca catggacaag attgttatcg tgggaatggc aaaaattata   1740
tgggcaactt atcccaaaca agatctggac taacatgttc aatgtgggac aagaacatgg   1800
aagacttaca tcgtcatatc ttctgggaac cagatgcaag taagctgaat gagaattact   1860
gccgaaatcc agatgatgat gctcatggac cctggtgcta cacgggaaat ccactcattc   1920
cttgggatta ttgccctatt tctcgttgtg aaggtgatac cacacctaca atagtcaatt   1980
tagaccatcc cgtaatatct tgtgccaaaa cgaaacaatt gcgagttgta aatgggattc   2040
caacacgaac aaacatagga tggatggtta gtttgagata cagaaataaa catatctgcg   2100
gaggatcatt gataaaggag agttgggttc ttactgcacg acagtgtttc ccttctcgag   2160
acttgaaaga ttatgaagct tggcttggaa ttcatgatgt ccacggaaga ggagatgaga   2220
aatgcaaaca ggttctcaat gtttcccagc tggtatatgg ccctgaagga tcagatctgg   2280
ttttaatgaa gcttgccagg cctgctgtcc tggatgattt tgttagtacg attgatttac   2340
ctaattatgg atgcacaatt cctgaaaaga ccagttgcag tgtttatggc tggggctaca   2400
```

-continued

```
ctggattgat caactatgat ggcctattac gagtggcaca tctctatata atgggaaatg   2460

agaaatgcag ccagcatcat cgagggaagg tgactctgaa tgagtctgaa atatgtgctg   2520

gggctgaaaa gattggatca ggaccatgtg agggggatta tggtggccca cttgtttgtg   2580

agcaacataa aatgagaatg gttcttggtg tcattgttcc tggtcgtgga tgtgccattc   2640

caaatcgtcc tggtattttt gtccgagtag catattatgc aaaatggata cacaaaatta   2700

ttttaacata taaggtacca cagtcatag                                     2729
```

What is claimed is:

1. A method for co-expressing two heterotypes of Hepatocyte Growth Factor (HGF) *in vivo in a mammalian subject with ischemic disease in order to treat the disease,* comprising*:* transforming or transfecting [to] *a DNA construct into* a cell *of a mammalian subject with ischemic disease by administering* a *DNA construct to the subject, the* DNA construct comprising:

(a) a promoter, (b) a first cDNA which has the same sequence as exons 1-4 of the human HGF gene wherein said exons 1-4 are arranged in sequential order without an intron therebetween, or degenerates thereof which do not alter the amino acid sequence encoded by said first cDNA, (c) a polynucleotide that has the same sequence as intron 4 of the HGF gene or a functional fragment thereof, and (d) a second cDNA which has the same sequence as exons 5-18 of the human HGF gene wherein said exons 5-18 are arranged in sequential order without an intron therebetween, or degenerates thereof which do not alter the amino acid sequence encoded by said second cDNA;

wherein (c) is located between (b) and (d); and the HGF construct simultaneously encodes two heterotypes of human HGF*, and*

*whereby two heterotypes of human HGF are co-expressed within the mammalian subject, thereby treating the ischemic disease.*

2. The method of claim 1, wherein said intron has the same sequence as a fragment of intron 4 of the HGF gene.

3. The method of claim 2, wherein the construct comprises a nucleotide sequence not less than 90% identical to SEQ ID NO: 19.

4. The method of claim 3, wherein the construct comprises a nucleotide sequence not less than 95% identical to SEQ ID NO: 19.

5. The method of claim 4, wherein the construct comprises the sequence of SEQ ID NO: 19.

6. The method of claim 2, wherein the construct comprises a nucleotide sequence not less than 90% identical to SEQ ID NO: 20.

7. The method of claim 6, wherein the construct comprises a nucleotide sequence not less than 95% identical to SEQ ID NO: 20.

8. The method of claim 7, wherein the construct comprises the sequence of SEQ ID NO: 20.

9. The method of claim 2, wherein the construct comprises a nucleotide sequence not less than 90% identical to SEQ ID NO: 21.

10. The method of claim 9, wherein the construct comprises a nucleotide sequence not less than 95% identical to SEQ ID NO: 21.

11. The method of claim 10, wherein the construct comprises the sequence of SEQ ID NO: 21.

12. The method of claim 1, wherein the one intron has the same sequence as the full intron 4 of the HGF gene.

13. The method of claim 1, wherein the construct comprises a nucleotide sequence not less than 90% identical to SEQ ID NO: 2.

14. The method of claim 13, wherein the construct comprises a nucleotide sequence not less than 95% identical to SEQ ID NO: 2.

15. The method of claim 14, wherein the construct comprises the sequence of SEQ ID NO: 2.

16. The method of claim 1, wherein the construct further comprises a terminator sequence, a self-replication sequence, or a secretory signal.

17. The method of claim 1, wherein the expression efficiency of the construct is higher than the expression efficiency of HGF cDNA or deleted variant HGF (dHGF) cDNA.

18. The method of claim 1, wherein the expression level of the construct is about 20- to 100-fold higher than the expression level of the HGF cDNA or dHGF cDNA.

[19. The method of claim 1, wherein the cell is a mammalian cell, a bacterial cell or a yeast cell.]

[20. The method of claim 19, wherein the cell is a mammalian cell.]

[21. The method of claim 20, wherein the transformation of said mammalian cell is in vivo.]

* * * * *